United States Patent
Hakonarson et al.

(10) Patent No.: US 11,401,553 B2
(45) Date of Patent: Aug. 2, 2022

(54) COMPOSITIONS AND METHODS FOR THE DIAGNOSIS AND TREATMENT OF LYMPHATIC SYSTEM DISORDERS

(71) Applicant: THE CHILDREN'S HOSPITAL OF PHILADELPHIA, Philadelphia, PA (US)

(72) Inventors: Hakon Hakonarson, Malvern, PA (US); Dong Li, Drexel Hill, PA (US); Lifeng Tian, Wilmington, DE (US); Kenny Nguyen, Aberdeen, NJ (US); Patrick Sleiman, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 229 days.

(21) Appl. No.: 16/327,060

(22) PCT Filed: Aug. 30, 2017

(86) PCT No.: PCT/US2017/049453
§ 371 (c)(1),
(2) Date: Feb. 21, 2019

(87) PCT Pub. No.: WO2018/045078
PCT Pub. Date: Mar. 8, 2018

(65) Prior Publication Data
US 2020/0056238 A1   Feb. 20, 2020

Related U.S. Application Data

(60) Provisional application No. 62/382,147, filed on Aug. 31, 2016.

(51) Int. Cl.
| | | |
|---|---|---|
| *C12Q 1/68* | (2018.01) | |
| *C12Q 1/6883* | (2018.01) | |
| *A61P 43/00* | (2006.01) | |
| *A61K 31/4184* | (2006.01) | |
| *A61K 31/436* | (2006.01) | |
| *A61K 31/4427* | (2006.01) | |
| *A61K 31/4709* | (2006.01) | |
| *A61K 31/501* | (2006.01) | |
| *A61K 31/519* | (2006.01) | |
| *A61K 31/5377* | (2006.01) | |
| *A61K 45/06* | (2006.01) | |

(52) U.S. Cl.
CPC ........ *C12Q 1/6883* (2013.01); *A61K 31/4184* (2013.01); *A61K 31/436* (2013.01); *A61K 31/4427* (2013.01); *A61K 31/4709* (2013.01); *A61K 31/501* (2013.01); *A61K 31/519* (2013.01); *A61K 31/5377* (2013.01); *A61P 43/00* (2018.01); *A61K 45/06* (2013.01); *C12Q 2600/156* (2013.01)

(58) Field of Classification Search
CPC ... C12Q 1/6883; C12Q 2600/156; C12Q 1/68
See application file for complete search history.

(56) References Cited

U.S. PATENT DOCUMENTS

| 10,835,513 B2 | 11/2020 | Silva et al. |
| 2012/0293130 A1 | 11/2012 | Burstein et al. |
| 2020/0024666 A1 | 1/2020 | Greene et al. |

FOREIGN PATENT DOCUMENTS

| WO | 2015/054280 A1 | 4/2015 |
| WO | 2015/095825 A1 | 6/2015 |

OTHER PUBLICATIONS

Nelson et al., "Somatic activating ARAF mutations in Langerhans cell histiocytosis", (2014) Blood 123(20): 3152-3155 (Year: 2014).*
Edelweiss et al., "Lymph node involvement by Langerhans cell histiocytosis: a clinicopathologic and immunohistochemical study of 20 cases", (2007) Human Path 38:1463-1469 (Year: 2007).*
Notice of Reasons for Rejection, dated Jul. 13, 2021, issued in corresponding Japanese Application No. 2019-511562, with English translation.
Civallero, Monica et al., "Activity of BKM120 and BEZ235 against Lymphoma Cells," BioMed Research International, vol. 2015, Article ID 870918, 2015, pp. 1-12.
Martin-Almedina, Silvia et al., "EPHB4 kinase-inactivating mutations cause autosomal dominant lymphatic-related hydrops fetalis," The Journal of Clinical Investigation, vol. 126, No. 8, Aug. 2016, pp. 3080-3088.
Ricci, K. W. et al., "A Phase 2 Clinical Trial Assessing Efficacy and Safety of the Mtor Inhibitor Sirolimus in the Treatment of Generalized Lymphatic Anomaly, Kaposiform Lymphangiomatosis, and Gorham-Stout Disease," American Journal of Respiratory and Critical Care Medicine, vol. 191, 2015, p. A5454.
Adams, D. et al., "Efficacy and Safety of Sirolimus in the Treatment of Complicated Vascular Anomalies", Pediatrics, 137(2): e20153257, pp. 1-10 (Feb. 2016).
Araujo, Aline N. et al., "Genome-Wide Copy Number Analysis in a Family with p.G533C RET Mutation and Medullary Thyroid Carcinonma Identified Regions Potentially Associated with a Higher Predisposition to Lynph Node Metastasis", J. Clin. Endocrinol. Metab., Mar. 2014.
Brouillard, P. et al., "Genetics of lymphatic anomalies", J. Clin. Invest., 124: 898-904 (2014).
Burrows, P.E., "Lymphatic anomalies are are associated with RASA1 gene mutations in mouse and man", 45: 167-171 (2010).
Faul, J.L. et al., "Thoracic lymphangionas, lymphangiectasis, lymphangiomatosis, and lymphatic dysplasia syndrome", Am. J. Respir. Crit. Care Med., 161: 1037-1046 (2000).
Hashimoto, T. et al., "Membrane-mediated regulation of vascular identity", Birth Defects Res. C Embryo Today, 108: 65-84 (2016).
Joyce, S. et al., "The lymphatic phenotype in Noonan and Cardiofaciocutaneous syndrome", Eur. J. Hum. Genet., 24: 690-696 (2016).

(Continued)

*Primary Examiner* — Jehanne S Sitton

(74) *Attorney, Agent, or Firm* — Kathleen D. Rigaut; Howson & Howson LLP

(57) ABSTRACT

Compositions and methods for the diagnosis and treatment of lymphatic anomaly are disclosed.

11 Claims, 14 Drawing Sheets

Specification includes a Sequence Listing.

(56) References Cited

OTHER PUBLICATIONS

Kawai, K. et al., "Tissue-specific Carcinogenesis in Transgenic Mice Expressing the RET Proto-Oncogene with a Multiple Endocrine Neoplasia Type 2A Mutation", Can. Res., 60: 5254-5260 (2000).

Kawasaki, J. et al., "RASA1 functions in EPHB4 signaling pathway to suppress endothelial mTORC1 activity", The Journal of Clinical Investigation, 124(6): 2774-2784 (2014).

Kettleborough, R.N. et al., "A systematic genome-wide analysis of zebrafish protein-coding gene function", Nature, 496: 494-497 (2013).

Kume, T., "Specification of arterial, venous, and lymphatic endothelial cells during embryonic development", Histol. Histopathol., 25: 637-646 (2010).

Kurek, V.L. et al., "Somatic mosaic activating mutations in PIK3CA cause CLOVES syndrome", Am. J. Hum. Genet., 90: 1108-1115 (2012).

Li, Dong et al., "Whole Exome Sequencing Identifies EPHB4 as a Novel Cause of Autosomal Dominant Lymphangiomatosis", ACMG Annual Clinical Genetics Meeting, Mar. 2015, pp. 1-2.

Lindhurst, M.J. et al., "A mosaic activating mutation in AKT1 associated with the Proteus syndrone", N. Engl. J. Med., 365: 611-619 (2011).

Luks, V.L. et al., "Lymphatic and other vascular malformative/overgrowth disorders are caused by somatic mutations in PIK3CA", J. Pediatr., 166: 1048-1054, e1041-1045 (2015).

Makinen, T. et al., PDZ interaction site in ephrinB2 is required for the remodeling of lymphatic vasculature, Genes Dev., 19: 397-410 (2005).

Sun, S. et al., Constitutive Activation of mTORC1 in Endothelial Cells Leads to the Development and Progression of Lymphangiosarcoma through VEGF Autocrine Signaling, Cancer Cell, 28: 758-772 (2015).

Wassef, M., "Vascular Anomalies Classification: Recommendations from the International Society for the Study of Vascular Anomalies", Pediatrics, 136: e203-214 (2015).

International Search Report/Written Opinion, dated Jan. 22, 2018, issued in corresponding International Application No. PCT/US17/49453, filed Aug. 30, 2017.

Alitalo, Kari et al., "Lymphangiogenesis in development and human disease," Nature, vol. 438, No. 7070, 2005, pp. 946-953.

Trenor, Cameron C. et al., "Complex lymphatic anomalies," Seminars in Pediatric Surgery, vol. 23, No. 4, 2014, pp. 186-190.

Lo et al., "Severe neonatal manifestations of Costello syndrome," Journal of Medical Genetics, vol. 45, No. 3, 2008, pp. 167-171.

Fabretto, Antonella et al., "Two cases of Noonan syndrome with severe respiratory and gastroenteral involvement and the SOS1 mutation F623I," European Journal of Medical Genetics, vol. 53, No. 5, 2010, pp. 322-324.

Morcaldi, G. et al., "Lymphodysplasia and KRAS Mutation: A Case Report and Literature Review," Lymphology, vol. 48, 2015, pp. 121-127.

Revencu, Nicole et al., "RASA1 Mutations and Associated Phenotypes in 68 Families with Capillary Malformation-Arteriovenous Malformation," Human Mutation, vol. 34, No. 12, 2013, pp. 1632-1641.

Smeltzer, D.M. et al., "Primary lymphatic dysplasia in children: chylothorax, chylous ascites, and generalized lymphatic dysplasia," European Journal of Pediatrics, vol. 145, 1986, pp. 286-292.

\* cited by examiner

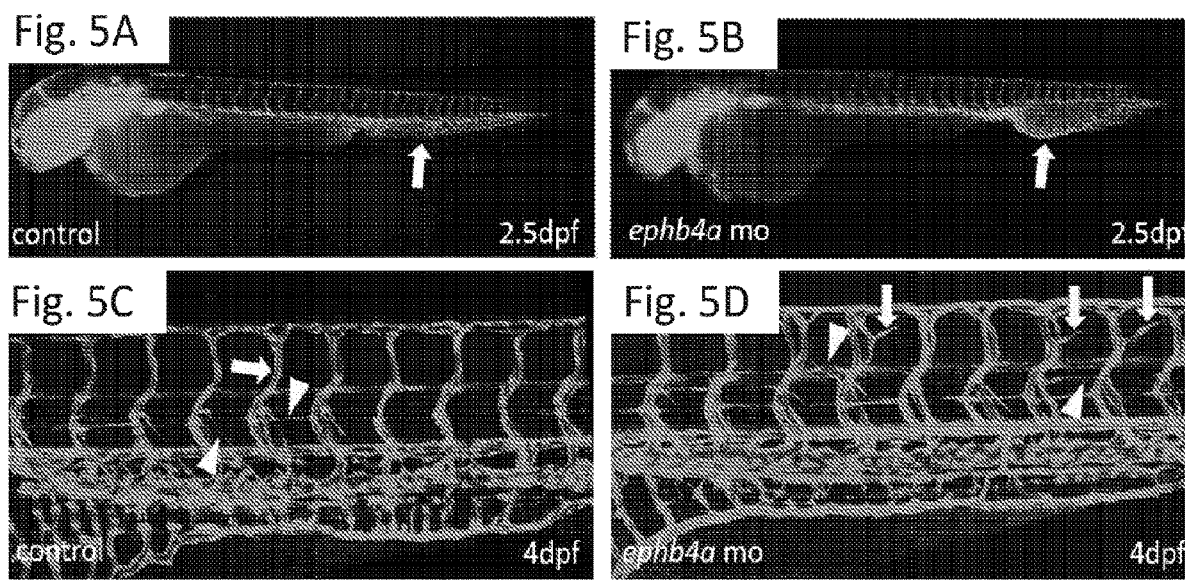

caudal rescue Rapamycin 2.5dpf branching rescue Rapamycin 4dpf branching rescue BEZ-235, 4dpf

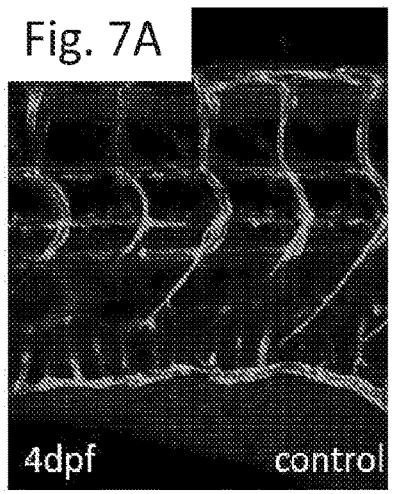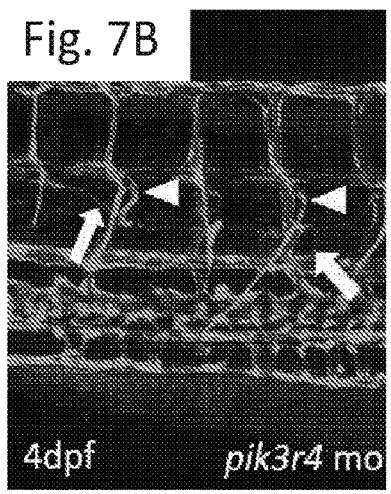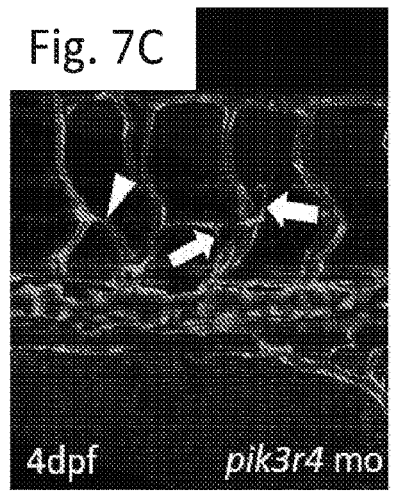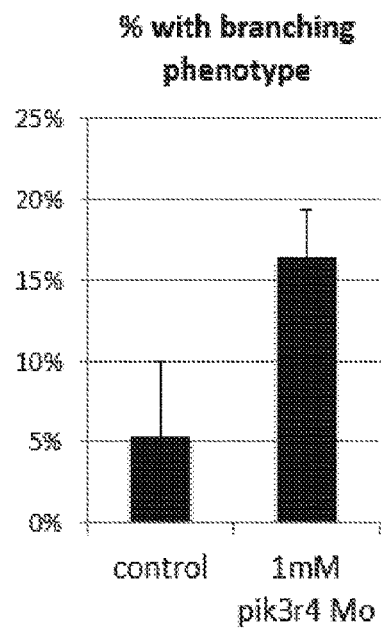

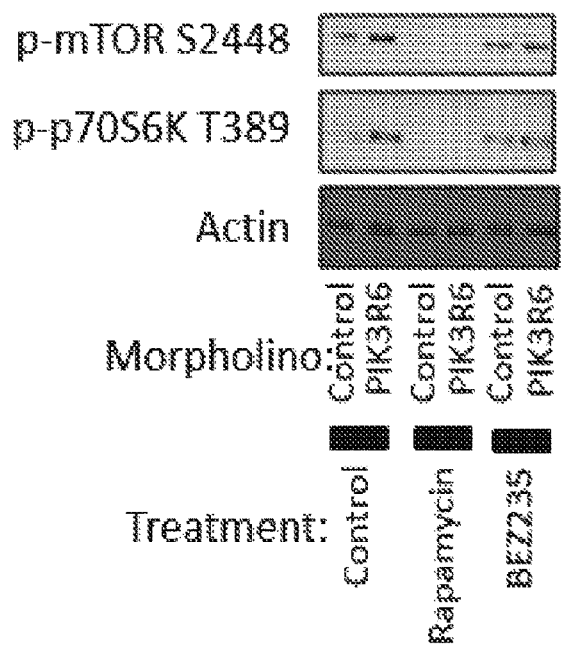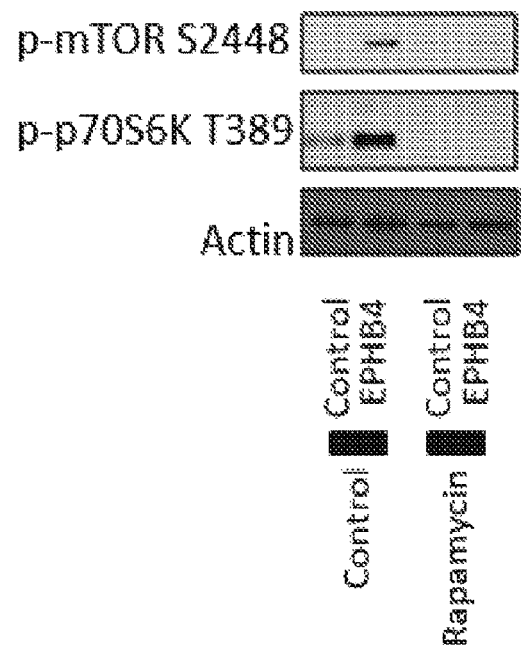

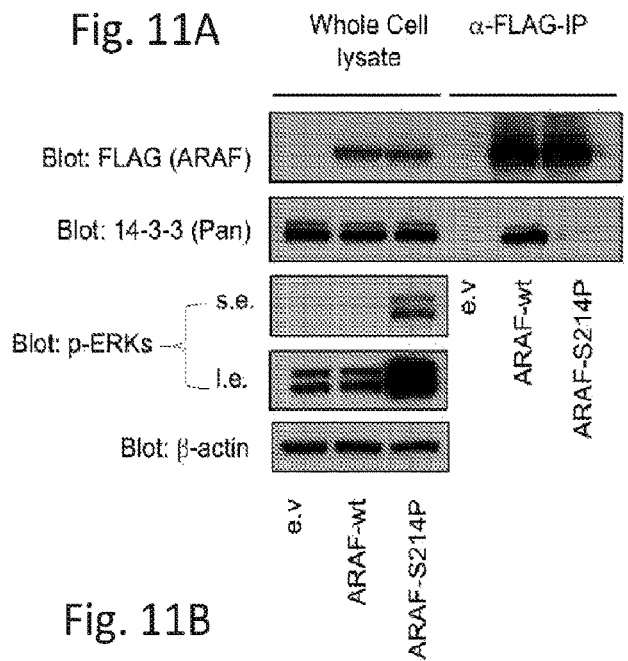
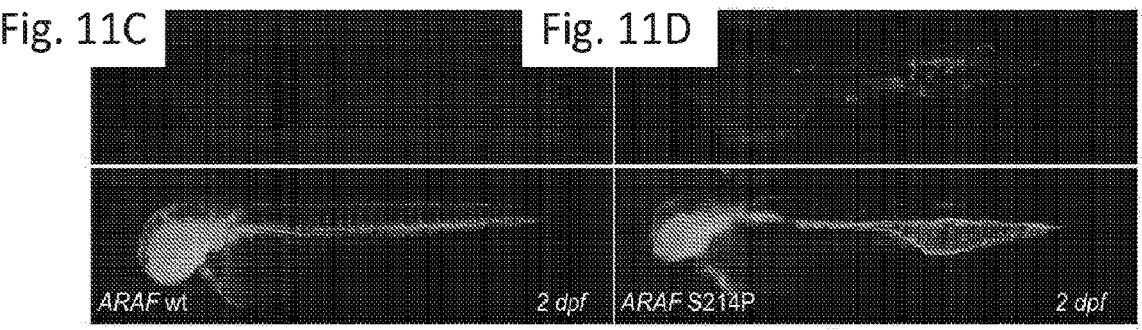
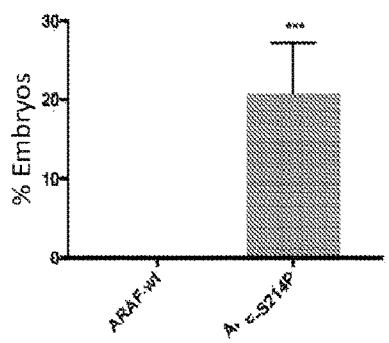
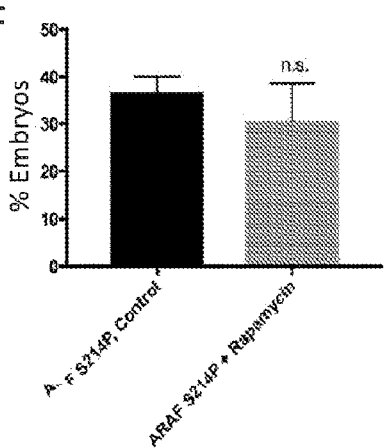

COMPOSITIONS AND METHODS FOR THE DIAGNOSIS AND TREATMENT OF LYMPHATIC SYSTEM DISORDERS

CROSS-REFERENCE TO RELATED APPLICATIONS

This application is a 071 of International Application No. PCT/US2017/049453, filed Aug. 30, 2017, which claims priority to U.S. Provisional Application No. 62/382,147, filed Aug. 31, 2017. The entire disclosure of each of the aforesaid applications is incorporated by reference in the present application.

INCORPORATION BY REFERENCE OF MATERIAL SUBMITTED IN ELECTRONIC FORM

Applicant hereby incorporates by reference the Sequence Listing material filed in electronic form herewith. This file is labelled "HakonarsonSeq_ST25.txt", dated Oct. 8, 2019 and is 3,572 bytes in size.

FIELD OF THE INVENTION

This invention relates to the fields of genetics, personalized medicine and malformations of the lymphatic system. More specifically the invention provides new genetic targets and therapeutic treatment regimens for amelioration of symptoms associated with Lymphangiomatosis and other generalized lymphatic anomalies (GLAs).

BACKGROUND OF THE INVENTION

Several publications and patent documents are cited throughout the specification in order to describe the state of the art to which this invention pertains. Each of these citations is incorporated by reference herein as though set forth in full.

The lymphatic system plays a pivotal role in maintaining the body fluid circulation, defending the body against disease and in absorbing dietary fats in the small intestine (1). Complex lymphatic anomalies are characterized by abnormal formation of lymphatic vessels and tissue overgrowth. Patients often present with overlapping symptoms which may lead to serious pulmonary disease (2, 3). Examples of lymphatic anomalies include generalized lymphatic anomaly (GLA), lymphangiectasia, and chylous effusions (pericardial, pleural or peritoneal). Research on complex lymphatic anomalies has been hampered by the inconsistence in classification and nomenclature because of significant challenge in diagnosis (3-6). Although the molecular genetic etiology of complex lymphatic anomalies is poorly understood, congenital malformations of lymphatic system appear to have related underlying genetic etiology (7-9). Indeed, both germline and somatic mutations have been identified in genes which converge on the PI3K/mTOR and Ras/MAPK pathways (1, 8).

Disruption or aberrations of the PI3K/mTOR and Ras/MAPK signaling pathways have been shown to impair normal expansion and remodeling during construction of a mature lymphatic network, wherein such disruptions are associated with lymphatic disease. Gain of function mutations in AKT1 and PIK3CA, resulting in elevated mammalian target of rapamycin complex 1 (mTORC1) activity, were identified in patients with lymphatic malformations that comprise part of a syndrome, such as Proteus syndrome (OMIM 176920), CLOVES syndrome (OMIM 612918) and Klippel-Trenaunay-Weber syndrome (OMIM 149000) (9-11). Mutations in KRAS, HRAS, RAF1, PTPN11, SOS1 and RASA1, resulting in dysregulated RAS pathway activity, cause lymphedema or lymphangiectasia in Noonan syndrome (OMIM 163950), Costello syndrome (OMIM 218040), cardiofaciocutaneous syndrome (OMIM 115150) and capillary malformation-arteriovenous malformation (CM-AVM) syndrome (OMIM 608354) (12-17).

Despite these understandings, genetic biomarkers for use in identifying patients with lymphatic disorders and lymphatic anomalies, such as lymphangiomatosis/lymphangiectasia (LAM), generalized lymphatic anomaly (GLA), and chylous effusions are lacking, as are therapeutics that target the genetic markers associated with these disorders.

SUMMARY OF THE INVENTION

Members from a three-generation family were analyzed using exome sequencing (ES) in search for novel germline mutations, as six individuals in the family were affected with lymphatic anomalies, including GLA, and significant venous stasis. A heterozygous germ-line mutation in EPHB4 was identified. EPHB4 knockdown studies in zebrafish confirmed that EPHB4 has a role in lymphatic vessel development and branching, a process involving mTOR signaling.

A cohort of 13 families with either GLA or lymphangiectasia diagnosis, all of whom had at least one family member with chylous effusion were sequenced. A homozygous variant in PIK3R6, which encodes the regulatory subunit of PI3K complex, a heterozygous mutation in MTOR, a heterozygous mutation in PIK3R4, and a recurrent de novo gain-of-function mutation in ARAF, which is involved in Ras/MAPK pathway, an interactor of the mTOR pathway were identified.

Accordingly, in one embodiment of the invention, a method for diagnosing a lymphatic anomaly in a human patient is provided. An exemplary method comprises obtaining a biological sample comprising nucleic acid from the patient. assaying the nucleic acid to determine whether i) a single nucleotide variant (SNV) in one or more of EPHB4, PIK3R4, PIK3R6, mTOR, and ARAF is present or ii) an SNV in linkage disequilibrium with an SNV in one or more of EPHB4, PIK3R4, PIK3R6, mTOR, and ARAF is present; and diagnosing the patient with a lymphatic anomaly if an SNV of i) or ii) is present. In another aspect, a method for diagnosing a lymphatic anomaly in a human patient entails obtaining genotype sequence information from a human patient, assaying the nucleic acid to determine whether i) a single nucleotide variant (SNV) in one or more of EPHB4, PIK3R4, PIK3R6, mTOR, and ARAF is present or ii) an SNV in linkage disequilibrium with an SNV in one or more of EPHB4, PIK3R4, PIK3R6, mTOR, and ARAF is present; and diagnosing the patient with a lymphatic anomaly if an SNV of i) or ii) is present.

The invention also provides a method for treating a lymphatic anomaly in a human patient. An exemplary method comprises obtaining a biological sample comprising nucleic acid from the patient; assaying the nucleic acid to determine whether i) a single nucleotide variant (SANV) in one or more of EPHB4, PIK3R4, PIK3R6, mTOR, and ARAF is present or ii) an SNV in linkage disequilibrium with an SNV in one or more of EPHB4, PIK3R4, PIK3R6, mTOR, and ARAF is present; and administering one or more agents suitable for treatment of said lymphatic anomaly to the patient identified as having one or more SNVs of i) or ii), thereby treating the lymphatic anomaly. In alternative embodiment of this method, genotype information is obtained from a patient and assayed to determine whether i) a single nucleotide variant (SNV) in one or more of EPHB4, PIK3R4, PIK3R6, mTOR, and ARAF is present or ii) an SNV in linkage disequilibrium with an SNV in one or more of EPHB4, PIK3R4, PIK3R6, mTOR, and ARAF is present; and administering one or more agents suitable for treatment of said lymphatic anomaly to the patient identified as having one or more SNVs of i) or ii), thereby treating the lymphatic anomaly. In alternative embodiment of this method, genotype information is obtained from a patient.

In certain embodiments, the lymphatic anomaly is characterized by abnormal formation of lymphatic vessels and/or tissue overgrowth. In other embodiments, the lymphatic anomaly is lymphangiomatosis (LAM). In another embodiment, the lymphatic anomaly is generalized lymphatic anomaly (GLA). The lymphatic anomaly can be characterized by chylous effusions, including pericardial, pleural, or peritoneal effusions.

The diagnostic methods can further comprise generating a report identifying the SNV after detection in the biological sample. The methods of treatment described above can further comprise generating a report identifying suggested treatment(s) for the lymphatic anomaly based upon the SNV identified in the method.

In yet another embodiment, the diagnostic methods described herein can further comprise administering an effective amount of one or more agents suitable for treating said lymphatic anomaly to the diagnosed patient.

In certain embodiments of the methods for treatment, the agent to be administered to patients harboring one or more lymphatic anomaly associated SNVs is selected from one or more mTOR inhibitors, one or more PIK3K inhibitors, one or more MEK/ERK inhibitors, and a combination of one or more of any of said inhibitors. In other embodiments, the agents or said inhibitors are listed in Tables 1 and 2. In some embodiments, when the agent is an mTor inhibitor, rapamycin and or BEZ-235 (dactolisib) is administered. In certain embodiments, the one or more mTOR inhibitors, one or more PIK3K inhibitors, and/or one or more MEK/ERK inhibitors has an IC50 of less than 100 μM, less than 10 μM, less than 1 μM, less than 100 nM, less than 10 nM, or less than 1 nM.

In another aspect of the invention, the agent that inhibits mTOR signaling also has additional biological activity. These include, without limitation, inhibition of PI3K, inhibition of FK506 binding protein, inhibition of DNA-PK, inhibition of p110, or inhibition of p70S6K. In some embodiments, the patient has one, two, three, four, or five SNVs in each of EPHB4, PIK3R4, PIK3R6, mTOR, and ARAF. In some embodiments, the patient does not have an SNV in EPHB4. In some embodiments, the patient does not have an SNV in PIK3R4. In some embodiments, the patient does not have an SNV in PIK3R6. In some embodiments, the patient does not have an SNV in mTOR. In some embodiments, the patient does not have an SNV in ARAF.

In some embodiments, the agents listed in Tables 1 and 2 are used in combination. These combinations include, without limitation, a) Ridaforolimus and Trametinib; b) Ridaforolimus and Selumetinib or Cobimetinib; c) BEZ235 and Selumetinib; d) Omipalisib and Selumetinib or Trametinib; e) Everolimus and Trametinib or Selumetinib; f) Sirolimus, Ridaforolimus and Selumetinib; g) Sirolimus, Ridaforolimus and Trametinib; h) Torkinib and Trametinib; i) BEZ235, Torkinib and Trametinib; and j) Sirolimus and Gedatolisib and Trametinib. In other embodiments, the treatment further comprises administering systemic chemotherapy, interferon alfa, radiotherapy, and/or surgery.

In some embodiments, the SNV is selected from c.2334+1G>C in EPHB4; c.3481A>G:p.S1161G in PIK3R4; c.1393-7C>T in PIK3R6; c.6818A>G:p.P2273L in mTOR; and c.640T>C:p.S214P in ARAF.

In some embodiments, the diagnostic method comprises detection of c.2334+1G>C in EPHB4. In some embodiments, the diagnostic method further comprises treating said patient with one or more agents selected from one or more mTor inhibitors, one or more PI3K inhibitor and one or more MEK/ERK inhibitors. In other embodiments, the agents are selected from Tables 1-2, thereby improving one or more of lymph structure, decreasing chylous pleural effusions, improving respiratory function, allowing tapering of concomitant medication usage, or increasing survival.

In some embodiments, the diagnostic method comprises detecting c.2334+1G>C in EPHB4 and administering at least one or more mTor inhibitors, one or more PI3K inhibitors and one or more MEK/ERK inhibitors alone or in combination. In other embodiments, the agent is selected from Tables 1-2, thereby improving one or more of lymphatic structure, decreasing chylous pleural effusions, improving respiratory function, allowing tapering of concomitant medication usage, or increasing survival.

In some embodiments, the diagnostic method comprises detection of c.3481A>G:p.S1161G in PIK3R4. In some embodiments, the diagnostic method further comprises treating said patient with one or more mTor inhibitors, one or more PI3K inhibitors and one or more MEK/ERK inhibitors alone or in combination. In other embodiments, agents are selected from Tables 1-2, thereby improving one or more of lymph structure, decreasing chylous pleural effusions, improving respiratory function, allowing tapering of concomitant medication usage, or increasing survival.

In some embodiments, the diagnostic method comprises detecting c.3481A>G:p.S1161G in PIK3R4 and administering one or more mTor inhibitors, one or more PI3K inhibitors and one or more MEK/ERK inhibitors alone or in combination. In other embodiments, at least one agent is selected from Tables 1-2 for administration, thereby improving one or more of lymphatic structure, decreasing chylous pleural effusions, improving respiratory function, allowing tapering of concomitant medication usage, or increasing survival.

In some embodiments, the diagnostic method comprises detection of c. 1393-7C>T in PIK3R6. In some embodiments, the diagnostic method further comprises treating said patient with one or more mTor inhibitors, one or more PI3K inhibitors and one or more MEK/ERK inhibitors alone or in combination. In other embodiments, agents from Tables 1-2 are selected, thereby improving one or more of lymph structure, decreasing chylous pleural effusions, improving respiratory function, allowing tapering of concomitant medication usage, or increasing survival.

In some embodiments, the diagnostic method comprises detecting c.1393-7C>T in PIK3R6 and administering one or more mTor inhibitors, one or more PI3K inhibitors and one or more MEK/ERK inhibitors alone or in combination. In some embodiments, at least one agent from Tables 1-2 is administered, thereby improving one or more of lymphatic structure, decreasing chylous pleural effusions, improving respiratory function, allowing tapering of concomitant medication usage, or increasing survival.

In some embodiments, the diagnostic method comprises detection of c.6818A>G:p.P2273L in mTOR. In some embodiments, the diagnostic method further comprises treating said patient with one or more mTor inhibitors, one or more PI3K inhibitors and one or more MEK/ERK inhibitors alone or in combination. In other embodiments, agents from Tables 1-2 are administered, thereby improving one or more of lymph structure, decreasing chylous pleural effusions, improving respiratory function, allowing tapering of concomitant medication usage, or increasing survival.

In some embodiments, the diagnostic method comprises detecting c.6818A>G:p.P2273L in mTOR and administering mTor inhibitors, one or more PI3K inhibitors and one or more MEK/ERK inhibitors alone or in combination. In other embodiments, at least one agent from Tables 1-2 is administered, thereby improving one or more of lymphatic structure, decreasing chylous pleural effusions, improving respiratory function, allowing tapering of concomitant medication usage, or increasing survival.

In some embodiments, the diagnostic method comprises detection of c.640T>C:p.S214P in ARAF. In some embodiments, the diagnostic method further comprises treating said patient with one or more mTor inhibitors, one or more PI3K inhibitors and one or more MEK/ERK inhibitors alone or in combination. In some embodiments, agents from Tables 1-2 are administered, thereby improving one or more of lymph structure, decreasing chylous pleural effusions, improving respiratory function, allowing tapering of concomitant medication usage, or increasing survival.

In some embodiments, the diagnostic method comprises detecting c.640T>C:p.S214P in ARAF and administering one or more mTor inhibitors, one or more PI3K inhibitors and one or more MEK/ERK inhibitors alone or in combination. In some embodiments, at least one agent from Tables 1-2 is administered, thereby improving one or more of lymphatic structure, decreasing chylous pleural effusions, improving respiratory function, allowing tapering of concomitant medication usage, or increasing survival. In subject having an SNV in ARAF, the agent is an ERK/MEK inhibitor. ERK/MEK inhibitors suitable for treatment include, without limitation, from Selumetinib (AZD6244). PD0325901, Trametinib (GSK1120212), PD184352 (CI-1040), Pimasertib (AS-703026), TAK-733, AZD8330, Binimetinib (MEK162, ARRY-162, ARRY-438162), SL-327, Refametinib (RDEA119, Bay 86-9766), and Cobimetinib (GDC-0973, RG7420).

In some embodiments, the step of assaying the nucleic acid to determine whether a single nucleotide variant (SNV) in one or more of EPHB4, PIK3R4, PIK3R6, mTOR, and ARAF is present further comprises the step of analyzing a polynucleotide sample to determine the presence of said SNV by performing a process selected from the group consisting of detection of specific hybridization, measurement of allele size, restriction fragment length polymorphism analysis, allele-specific hybridization analysis, single base primer extension reaction, and sequencing of an amplified polynucleotide.

In some embodiments, the biological sample comprises DNA.

In some embodiments, the biological sample comprises RNA.

In some embodiments, nucleic acids comprising said SNV(s) are obtained from an isolated cell of the human patient.

In some embodiments, an isolated vector encodes a nucleic acid with a SNV, wherein the SNV is selected from c.2334+1G>C in EPHB4; c.3481A>G:p.S1161G in PIK3R4; c.1393-7C>T in PIK3R6; c.6818A>G:p.P2273L in mTOR; and c.640T>C:p.S214P in ARAF.

In some embodiments, a host cell comprises an isolated vector encoding a nucleic acid with a SNV. In some embodiments, a transgenic animal comprises a host cell. In some embodiments, the transgenic animal is a mouse or zebrafish.

In some embodiments, a method of screening for effects of an agent comprises contacting a host cell or a transgenic animal with one or more of an mTor inhibitors, one or more PI3K inhibitors and one or more MEK/ERK inhibitors alone or in combination, or an agent from Tables 1-2 is encompassed. In some embodiments, the effect of an agent that is screened is caudal rescue or branching rescue in zebrafish. In some embodiments, the effect of an agent that is screened is phosphorylation of mTOR.

In some embodiments, a method for identifying an agent that alters cellular signaling, comprises providing cells expressing at least one nucleic acid comprising at least one SNV as described above, providing cells which express the cognate wild type sequences lacking the SNV; contacting both cell populations with a test agent; and analyzing whether said agent alters cellular signaling of cells harboring the SNV containing nucleic acid relative to cells lacking said SNV.

BRIEF DESCRIPTION OF THE DRAWINGS

In FIG. 3A, 293T cells were transiently transfected with wild type EPHB4 alone, mutant EPHB4 alone, or the mixtures of the wild type and mutant in the indicated ratios. Lysates were separated by SDS-PAGE and blotted for phosphotyrosine (pTyr, top) or EPHB4 (bottom). In FIG. 3B, A375 cells were transfected with wild type EPHB4, mutant EPHB4, or left untransfected. Cells were stimulated with either plate-bound Ephrin B2 Fc or human IgG as a control. Cells were lysed, and transfected proteins were immunoprecipitated. Immunoprecipitations were blotted for phosphotyrosine (top) or EPHB4 (middle). Whole cell lysates were blotted for EPHB4 to demonstrate equal expression (bottom).

FIGS. 5A-5H. ephb4a knock-down induces mTOR signaling dependent expansion of the caudal vascular plexus and mis-guided vessels in the intersomitic vasculature. Morpholino mediated knock-down of ephb4a (FIG. 5B) induces expansion and fusion of the caudal vasculature on 2.5 dpf (arrowheads) compared to control (FIG. 5A). FIG. 5C shows that on 4 dpf the zebrafish vascular system consists of intersomitic blood vessels that project in dorso-ventral direction (arrow) as well as thinner lymphatic vessels (arrowheads). The lymphatic parachordal line runs horizontally along the trunk (downward arrowhead) while the intersegmental lymphatic vessels project downwards (upward arrowhead). FIG. 5D shows that ephb4a knock down induces misguided vessels that resemble blood vessels (arrows) and lymphatic vessels (arrowheads). (FIGS. 5C and 5D are merged from 2 neighboring confocal scans) FIG. 5E shows defects in the caudal plexus are detected in 52% of ephb4a morpholino injected larvae at 2.5 dpf, and mis-branching vasculature is present in 46% on day 4. Rapamycin can significantly reduce the number of animals with defect on 2.5 dpf (FIG. 5F) and 4 dpf (FIG. 5G). FIG. 5H shows that BEZ-235 similarly rescues the branching defect on day 4.

FIGS. 6A (control) and 6B (pik3r6 morpholino) show morpholino mediated knock-down of pik3r6 induces mis-branching of vessels that resemble blood vessels (arrows) and lymphatic vessels (arrowheads) (panels are merged from 2 neighboring confocal scans). Trunk vessels defects could be induced by morpholinos targeting exon 4 (FIG. 6C) and exon 13 (FIG. 6D). Both rapamycin (FIG. 6E) and BEZ-235 (FIG. 6F) significantly reduced the number of larvae with vessel defects.

FIGS. 7A-7D. Morpholino mediated pik3r4 knock down induces mis-guided intersomitic vessels. Control injected larvae show normal vessel architecture at 4 dpf (FIG. 7A), while pik3r4 knock down induces mis-branching in vessels resembling blood (arrowheads) or lymphatic (arrows) vessels (FIGS. 7B-7C). FIG. 7D shows that defects were detected in only 5% of control-injected larvae but in 16% of pik3r4 morpholino injected larvae.

FIGS. 8A-8B. Overactive mTORC1 contributes to mis-branching phenotypes and mTOR inhibitors rescue the phenotype. FIG. 8A shows lysates from zebrafish larvae treated with either PIK3R6 morpholino or control morpholino, and untreated or treated with rapamycin or BEZ235 were separated by SDS-PAGE and blotted for phosphor-mTOR S2448 or phosphor-p70S6K T389. Blotting for beta-actin was used as a loading control. FIG. 8B shows that lysates from zebrafish larvae treated with either EPHB4 morpholino or control morpholino, and untreated or treated with rapamycin were separated by SDS-PAGE and blotted for phosphor-mTOR S2448 or phosphor-p70S6K T389. Blotting for beta-actin was used as a loading control.

FIGS. 11A to 11L. ARAF S214P mutation increased MAPKs activity, and overexpression of human ARAF mutant in zebrafish resulted in vasculature defects. (FIG. 11A) Cell lysates from HEK293T cells were transfected with FLAG-tagged wild type ARAF or S214P-ARAF mutant. Immunoprecipitation was performed using the anti-FLAG (M2) antibody, followed by Western blot using the antibodies indicated. Aliquots of the cell lysates were analyzed by Western blot. Activation was reflected by increased phosphorylation of ERKs through impaired association with 14-3-3 proteins. (FIG. 11B) Tg(fli1:ARAF-V2a-mCherry) line was generated using Tol2 gateway kit. Briefly, human S214P mutant or wild type ARAF cDNA was injected with a transposon donor plasmid containing Tol2 construct with a fli1 promoter. Transient mosaic expression was visualized by mCherry linked to ARAF by an autocatalytic V2a protein cleavage site. (FIG. 11C and FIG. 11D) Expression of human ARAF induced enlarged caudal vessels. (FIG. 11E) The enlarged caudal vessels defect was detected in 21% of transgenic expression of human ARAF S214P but not wild type at 2 dpf (* $P<0.001$). (FIG. 11F and FIG. 11G) mTORC1 inhibitor Rapamycin (FIG. 11F) and BEZ235 targeting both PI3K and mTORC1 (FIG. 11G) had no therapeutic effect on transient transgenic zebrafish (n.s., not significant). (FIG. 11H, FIG. 11I, and FIG. 11J) MEK inhibitory drugs, U0126 (FIG. 11H,  $P<0.01$), Cobimetinib (FIG. 11I,  $P<0.01$) and Selumetinib (FIG. 11J, * $P<0.001$), significantly reduced the number of larvae with expansion and fusion of the caudal vasculature at 2 dpf. (FIG. 11L and FIG. 11K) Transgenic expression of human ARAF S214P in zebrafish was found to severely affect the normal dorso/ventral vessel formation (FIG. 11L), while wild type ARAF expression had no effect (FIG. 11K).

SUMMARY OF SEQUENCES

Figure 1:
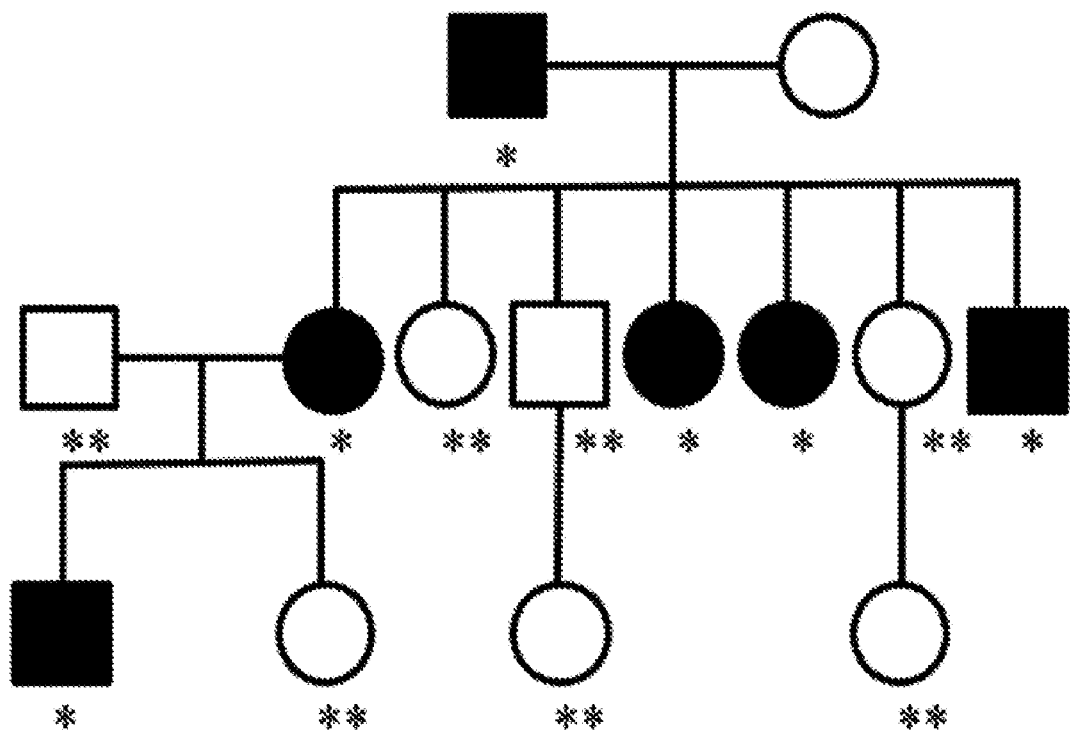
FIG. 1. Pedigree of Family-1 and cosegregating pattern of the EPHB4 mutation. The open circles denote unaffected females and the open squares denoted unaffected males; the solid figures indicate affected subjects. EPHB4 genotypes are noted beneath the symbol for each subject from whom DNA was available for testing.

The following SEQ ID table provides information on sequences used in this application.

| SEQ. ID No. | Description | Sequence |
| --- | --- | --- |
| 1 | Primer 1 for insertion into EPHB4 | TGGGAATCTT TCCTCCCCCC AGCATTAGCA GGGAGCTAGT GTAG |
| 2 | Primer 2 for insertion into EPHB4 | CTACACTAGC TCCCTGCTAA TGCTGGGGGG AGGAAAGATT CCCA |
| 3 | Forward amplification PCR primer | ATGAATTCGC CACCATGGAG CTCCGGGTGC TGCTC |

-continued

| SEQ. ID No. | Description | Sequence |
|---|---|---|
| 4 | Reverse amplification PCR primer | ATGCGGCCGC TCAGTACTGC GGGGCCGGTC C |
| 5 | Forward FLAG insertion primer | GATGATGATA AATTGGAAGA GACCCTGCTG AACAC |
| 6 | Reverse FLAG insertion primer | ATCTTTATAA TCAGCTGCAG CCAACGAAGC |
| 7 | EPHB4 gRNA | ggtcgtaatg gtccctcga |
| 8 | hEPHB4-F for assembly of gRNA | caccgCGAGC TCCCTGGTAA TGCTG |
| 9 | hEPHB4-R for assembly of gRNA | aaacCAGCAT TACCAGGGAG CTCGc |
| 10 | hPIK3R6-F for assembly of gRNA | caccgCTTCT GGGGGAAAGG GGAT |
| 11 | hPIK3R6-R for assembly of gRNA | aaacCATCCC CTTTCCCCCA GAAGc |
| 12 | hEPHB4 Single-stranded donor oligonucleotides | accctcagcc tcccacctttt ccaacctgcc ctgcccacct ggccctaaga agctcacacc cagtattacc cccagcatta gcaaagaact agtgtaggtg ggatcggaag agttctcctc caggaatcgg gaaaggccaa agtcagacac tttgcagacg aggttgctgt tgactagga |
| 13 | Primer 1 to generate P2273L mutant | GCGGATGGCT CTGGACTATG ACC |
| 14 | Primer 2 to generate P2273L mutant | AACATGATGC GATGCTCGAT GTTG |
| 15 | Morpholino sequence targeting exon 13 of EPHB4 | CGAGAGCAGTATTTACCAGTGAGCT |

DETAILED DESCRIPTION OF THE INVENTION

Whole exome sequencing on DNA samples obtained from a three-generation family, three being affected with lymphatic anomalies, was performed to identify the genetic basis of this previously unexplained rare disease. All missense, nonsense, splice-altering, and coding indel mutations that matched the autosomal dominant inheritance model of the family were examined. Results were filtered to exclude synonymous variants, variants with minor allele frequency (MAF) greater than 0.5%, and variants previously identified in controls. Relevant candidates were further analyzed. As a result, a single base pair substitution, c.2334+1G>C, that results in a splice site mutation within the EPHB4 gene was identified as a causal mutation. Samples from additional patients diagnosed with lymphatic anomalies were analyzed, and additional disease-causing SNVs were identified—a missense mutation in PIK3R3, a splicing mutation in PIK3R6, a missense mutation in MTOR, and mutation of a conserved phosphorylation site in ARAF.

These novel lymphatic anomaly-related SNVs are c.2334+1G>C in EPHB4, c.3481A>G:p.S1161G in PIK3R4, c.1393-7C>T in PIK3R6, c.6818A>G:p.P2273L in mTOR, and c.640T>C:p.S214P in ARAF. The SNVs of c.2334+1G>C in EPHB4, c.3481A>G:p.S1161G in PIK3R4, c.1393-7C>T in PIK3R6, c.6818A>G:p.P2273L in mTOR, and c.640T>C:p.S214P in ARAF may be referred to as "lymphatic anomaly-related SNVs" or "lymphatic anomaly-associated mutations" in this application.

Thus, the present disclosure encompasses methods for diagnosing lymphatic anomalies wherein a patient is diagnosed with lymphatic anomalies if they have at least one SNV in EPHB4, PIK3R3, PIK3R6, and mTOR as compared to a negative control, or have at least one SNV in linkage disequilibrium with at least one SNV in EPHB4, PIK3R4, PIK3R6, mTOR, and ARAF. The disclosure also encompasses methods for treating lymphatic anomalies in patients having at least one SNV in EPHB4, PIK3R3, PIK3R6, and mTOR with at least one mTOR inhibitor, at least one PIK3K inhibitor, and/or at least one MEK inhibitor (e.g., at least one agent listed in Tables 1-2).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, a compound "selected from the group consisting of" refers to one or more of the compounds in the list that follows, including mixtures (i.e., combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

"Lymphatic anomaly" refers to a disease or disorder characterized by abnormal formation of lymphatic vessels and tissue overgrowth. Non-limiting examples of lymphatic anomalies include "Lymphangiomatosis" or "lymphangiectasia" (referred to collectively herein as LAM), lymphangiomas, generalized lymphatic anomaly (GLA), and chylous effusions, generalized lymphangioma, systemic cystic angiomatosis, multiple lymphangiectasias, generalized lymphatic malformation, diffuse lymphatic malformation, Kaposiform LAM and Gorham-Stout disease (GSD), a rare vascular disorder of lymphatic origin characterized by progressive bone osteolysis.

Clinically, lymphangiomas are classified into several types. These include (1) Simplex, which is made up of capillary sized, thin-walled lymphatic channels. This type usually affects the skin (lymphangioma circumscriptum); (2) Cystic lymphangioma (or cystic hygroma): this may range in size from a few millimeters to several centimeters, seen in a young age, commonly in the neck or the axilla; (3) Cavernosum: this type is made up of dilated lymphatic channels, often with fibrous adventitial coats. This is the type which usually affects organs in the thorax, abdomen, and bones. Each of these lymphangiomas are encompassed in the invention.

A "single nucleotide variation (SNV)" refers to a position in genomic DNA where there is a single base that differs from the usual base at that position. An SNV is similar to an SNP except that an SNP generally refers to an SNV that occurs with some frequency (e.g., occurring in greater than a certain percentage of the population), whereas SNV provides no frequency information. Millions of SNV's have been cataloged in the human genome. Some SNVs are responsible for disease, while other SNVs are normal variations in the genome.

A "lymphatic anomaly-associated-SNV or -specific marker" is an SNV that is associated with an increased risk of developing a lymphatic anomaly, and is not found in patients who do not have this disease. Such markers may include, but are not limited to, nucleic acids, proteins encoded thereby, or other small molecules.

The term "genetic alteration," as used herein, refers to a change from the wild-type or reference sequence of one or more nucleic acid molecules. Genetic alterations include without limitation, SNVs and SNPs, copy number variations (CNVs), base pair substitutions, additions, and deletions of at least one nucleotide from a nucleic acid molecule of a known sequence.

"Linkage" describes the tendency of genes, alleles, loci or genetic markers to be inherited together as a result of their location on the same chromosome, and is measured by percent recombination (also called recombination fraction, or $\theta$) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

The term "solid matrix," as used herein, refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose. A solid matrix can comprise nucleic acids immobilized thereon such that they are not removable from the matrix in solution.

"Target nucleic acid," as used herein, refers to a previously defined region of a nucleic acid present in a complex nucleic acid mixture wherein the defined wild-type region contains at least one known nucleotide variation, which may or may not be associated with a lymphatic anomaly. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2- to 5-fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus, if a nucleic acid sequence contains the following sequence of bases: thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any lymphatic anomaly-specific marker nucleic acid, but does not hybridize to other nucleotides. Such markers include, for example the lymphatic anomaly-specific markers shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5°C + 16.6 \text{ Log } [Na+] + 0.41(\% G+C) - 0.63(\% \text{ formamide}) - 600/\# \text{ bp in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6× SSC, 5×Denhardt's solution, 0.5% SDS and 100 gig/ml denatured salmon sperm DNA at 42° C., and washed in 2× SSC and 0.5% SDS at 55° C. for 15 minutes. A high stringency hybridization is defined as hybridization in 6× SSC, 5×Denhardt's solution, 0.5% SDS and 100 µg/ml denatured salmon sperm DNA at 42° C., and washed in 1× SSC and 0.5% SDS at 65° C. for 15 minutes. A very high stringency hybridization is defined as hybridization in 6× SSC, 5×Denhardt's solution, 0.5% SDS and 100 gig/ml denatured salmon sperm DNA at 42° C., and washed in 0.1× SSC and 0.5% SDS at 65° C. for 15 minutes.

The term "oligonucleotide," as used herein, is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe," as used herein, refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe (in certain cases nucleic acids associated with a specified rs number associated with a single nucleotide polymorphism available in the dbSNP database) typically contains 15-25, 15-35, 20-50, or 100 or more nucleotides, although it may contain fewer nucleotides, provided the site of the SNV is included in the probe. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer," as used herein, refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25, 15-40, 20-50, etc. or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNAs of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting Lymphangiomatosis mRNA, for example, may be between 15-35 nucleotides in length, and more typically about 21 nucleotides in length.

The term "vector" relates to a single- or double-stranded circular nucleic acid molecule that can be infected, transfected or transformed into cells and replicate independently or within the host cell genome. A circular double-stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together. When cloning a genetic region containing a duplication or a deletion, the skilled artisan is well aware that flanking sequences upstream and downstream of the affected region of a suitable length (e.g., between 50-100 or more nucleotides) would be employed in the cloning process. Such vectors would have utility, for example in cell lines for studying the effects such alterations have on the encoded proteins.

Many techniques are available to those skilled in the art to facilitate transformation, transfection, or transduction of the expression construct into a prokaryotic or eukaryotic organism. The terms "transformation," "transfection," and "transduction" refer to methods of inserting a nucleic acid and/or an expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the lymphatic anomaly-specific marker nucleic acid molecule such that the latter is transcribed into mRNA. Host cell machinery then translates mRNA into a polypeptide. Promoter elements may drive constitutive or inducible expression of a coding region of interest.

Those skilled in the art will recognize that a nucleic acid vector can contain nucleic acid elements other than the promoter element and the lymphatic anomaly-specific marker encoding nucleic acid. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single- or double-stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system," "reporter gene," or "reporter gene product" shall mean an operative genetic system in which a nucleic acid comprises a gene that encodes a product that when expressed produces a reporter signal that is readily measurable, e.g., by biological assay, immunoassay, radio immunoassay, or by colorimetric, fluorogenic, chemiluminescent or other methods. The nucleic acid may be either RNA or DNA, linear or circular, single- or double-stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g., enhancers) in an expression vector.

The terms "recombinant organism" or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism. Example transgenic organisms include zebrafish or mice.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably a lymphatic anomaly-specific marker molecule, such as a marker shown in the tables provided below. Samples may include but are not limited to cells, body fluids, including blood, serum, plasma, urine, lymph, saliva, tears, pleural fluid and the like.

"Genotype sequence information" generally refers to any information related to the sequence of a subject's DNA or RNA. Genotype sequence information comprises whole genome, whole exome sequencing, exome sequencing, or targeted sequencing of areas of interest within the genome of a subject. Genotype sequence information may also include generation of data on the presence or absence of specific SNVs, such as those found herein to be associated with lymphatic anomalies. In addition, genotype sequence information would include use of probes to detect the presence of and/or expression of one or more lymphatic anomaly-associated SNVs. Examples of how probes may be used to obtain genotype sequence information include, but are not limited to: (1) in situ hybridization; (2) southern hybridization (3) northern hybridization; and (4) assorted amplification reactions such as polymerase chain reactions (PCR).

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNV containing nucleic acids described herein or their encoded proteins. Example agents include at least one mTOR inhibitor, at least one PIK3K inhibitor, and/or at least one MEK inhibitor. Example agents also include those listed in Tables 1-2. Agents are evaluated for potential biological activity by inclusion in screening assays described herein below.

"Treatment," as used herein, covers any administration or application of a therapeutic for disease in a mammal, including a human, and includes inhibiting the disease or progression of the disease, inhibiting or slowing the disease or its progression, arresting its development, partially or fully relieving the disease, preventing the onset of the disease, or preventing a recurrence of symptoms of the disease. Example treatments include administration at least one mTOR inhibitor, at least one PIK3K inhibitor, and/or at least one MEK inhibitor (e.g., at least one of the agents listed in Tables 1-2) at efficacious doses.

The terms "inhibition" or "inhibit" refer to a decrease or cessation of any event (such as protein ligand binding) or to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. It is not necessary that the inhibition or reduction be complete. For example, in certain embodiments, "reduce" or "inhibit" refers to the ability to cause an overall decrease of 20% or greater. In another embodiment, "reduce" or "inhibit" refers to the ability to cause an overall decrease of 50% or greater. In yet another embodiment, "reduce" or "inhibit" refers to the ability to cause an overall decrease of 75%, 85%, 90%, 95%, or greater.

The term "inhibitor" refers to an agent that slows down or prevents a particular chemical reaction, signaling pathway or other process, or that reduces the activity of a particular reactant, catalyst, or enzyme.

The terms "patient" and "subject" are used interchangeably to mean a mammal, including human.

The term "mTOR" refers to the mammalian target of rapamycin encoded by mTOR. mTOR may associate in complexes with other proteins to enable critical cellular functions. The term "mTORC" refers to the mammalian target of rapamycin complex 1, also known as mechanistic target to rapamycin complex 1, which is a protein complex that functions to activate translation of proteins. For example, mTORC1 comprises mTOR, regulatory-associated protein of mTOR (Raptor), mammalian lethal with SEC 13 protein 8 (MLST8), PRAS40, and DEPTOR. In another example, the mTORC2 complex comprises mTOR, rapamycin-insensitive companion of mTOR (RICTOR), GβL, mammalian stress-activated protein kinase interacting protein 1 (mSIN1), Protor 1/2, DEPTOR, TTI1, and TEL2. Any complex of proteins comprising mTOR may be referred herein as an mTORC. The term "mTOR signaling" would refer to the activity of mTOR, mTORC1, and MTORC2, along with other proteins that are known to interact in complexes with these proteins.

The term "mTORC inhibitor" refers to a class of agents that inhibit the mechanistic target of rapamycin (mTOR), which is a serine/threonine-specific protein kinase that belongs to the family of phosphatidylinositol-3 kinase (PI3K) related kinases (PIKKs). mTOR regulates cellular metabolism, growth, and proliferation by forming and signaling through two protein complexes, mTORC1 and mTORC2. The most established mTOR inhibitors are so-called rapalogs (rapamycin and its analogs). Several rapalogs are listed in Tables 1 and 2.

The term "PIK3K" or "PI3K" are used interchangeably herein to refer to phosphatidylinositol-4,5-bisphosphate 3-kinase (also called phosphatidylinositide 3-kinases, phosphatidylinositol-3-kinases, PI 3-kinases, PI(3)Ks, PI-3Ks. PI3K(s)) are a family of enzymes involved in cellular functions such as cell growth, proliferation, differentiation, motility, survival and intracellular trafficking, which in turn are involved in cancer. PI3Ks are signal transducer enzymes which regulate intracellular enzymes capable of phosphorylating the 3 position hydroxyl group of the inositol ring of phosphatidylinositol (PtdIns).

The term "PIK3K inhibitor" or "PI3K inhibitor" refers to a class of agents that function by inhibiting one or more of the phosphoinositide 3-kinase enzymes, which are part of the PI3K/AKT/mTOR pathway, an important signaling pathway for many cellular functions such as growth control, metabolism and translation initiation. Within this pathway there are many components, inhibition of which may result in tumor suppression. These anti-cancer drugs are examples of targeted therapy. There are a number of different classes and isoforms of PI3Ks. Class 1 PI3Ks have a catalytic subunit known as p110, with four types (isoforms)—p110 alpha, p110 beta, p110 gamma and p110 delta.

The term "MEK" refers to the MAPK/ERK pathway (also known as the Ras-Raf-MEK-ERK pathway) which comprise a chain of proteins in the cell that communicate a signal from a receptor on the surface of the cell to the DNA in the nucleus of the cell. The signal starts when a signaling molecule binds to the receptor on the cell surface and ends when the DNA in the nucleus expresses a protein and produces some change in the cell, such as cell division. The pathway includes many proteins, including MAPK (mitogen-activated protein kinases, originally called ERK, extracellular signal-regulated kinases), which communicate by adding phosphate groups to a neighboring protein, which acts as an "on" or "off" switch.

The term "MEK inhibitor" or "MEK/ERK inhibitor" refers to an agent that inhibits the mitogen-activated protein kinase enzymes MEK1, MEK2, and/or ERK. They can be used to affect the MAPK/ERK pathway which is often overactive in some cancers. The term "cellular signaling" would comprise mTOR signaling as well as any other signal transduction pathway process that governs cells homeostasis or activity.

Diagnosing Patients with Lymphatic Anomalies

In some embodiments, patients with lymphatic anomalies are diagnosed based on the presence of an SNV after obtaining genotype sequence information from a biological sample obtained from a patient. In some embodiments, patients with lymphatic anomalies are diagnosed based on detecting the presence of one or more SNV in a gene selected from EPHB4, PIK3R4, PIK3R6, mTOR, and ARAF, or an SNV in linkage disequilibrium with an SNV in a gene selected from EPHB4, PIK3R4, PIK3R6, mTOR, and ARAF associated with lymphatic anomaly. after obtaining genotype sequence information from a biological sample obtained from a patient. In some embodiments, this one or more SNV in a gene selected from EPHB4, PIK3R4, PIK3R6, mTOR, and ARAF is c.2334+1G>C in EPHB4; c.3481A>G:p.S1161G in PIK3R4; c.1393-7C>T in PIK3R6; c.6818A>G:p.P2273L in mTOR; or c.640T>C:p.S214P in ARAF.

In some embodiments, a report identifying the SNV(s) present in a particular subject may be generated from experimental data. In some embodiments, a report identifying suggested treatment(s) for the lymphatic anomaly may be generated based upon the data on SNV(s) identified using genotype sequence information.

In some embodiments, diagnosis based on detecting the presence of one or more SNV in a gene selected from EPHB4, PIK3R4, PIK3R6, mTOR, and ARAF, or an SNV in linkage disequilibrium with an SNV in a gene selected from EPHB4, PIK3R4, PIK3R6, mTOR, and ARAF, after obtaining genotype sequence information from a biological sample obtained from a patient guides the choice of treatment for the patient. In some embodiments, diagnosis based on detecting the presence of one or more SNV in a gene selected from EPHB4, PIK3R4, PIK3R6, mTOR, and ARAF, or an SNV in linkage disequilibrium with an SNV in a gene selected from EPHB4, PIK3R4, PIK3R6, mTOR, and ARAF, after obtaining genotype sequence information from a biological sample obtained from a patient does not guide or impact the choice of treatment for the patient.

In some embodiments, diagnosis of a lymphatic anomaly is made solely based on clinical presentation, scanning results, and/or family history. In some embodiments, diagnosis of a lymphatic anomaly is made without testing for genetic sequence information. In some embodiments, diagnosis of a lymphatic anomaly is made based on clinical presentation together with genetic sequence information.

The lymphatic anomaly-related SNVs disclosed in this invention can be used in a number of ways to diagnose lymphatic anomalies.

For example, nucleic acids comprising lymphatic anomaly-associated SNVs may be used as probes to detect the presence of and/or expression of lymphatic anomaly-specific markers. Methods in which lymphatic anomaly-associated marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting lymphatic anomaly-associated SNVs, or the proteins encoded thereby, may be conducted on any type of biological sample, including but not limited to body fluids (including blood, urine, serum, gastric lavage), any type of cell (such as brain cells, white blood cells, mononuclear cells) or body tissue.

Lymphatic anomaly-associated SNV-containing nucleic acids, vectors expressing the same, lymphatic anomaly-associated SNV-containing marker proteins and anti-lymphatic anomaly-specific marker antibodies can be used to detect lymphatic anomaly-associated SNVs in body tissue, cells, or fluid, and alter lymphatic anomaly-associated SNV-containing marker protein expression for purposes of detecting and diagnosing lymphatic anomalies.

Methods for detecting and/or diagnosing lymphatic anomalies based on lymphatic anomaly-associated SNVs are encompassed. The method may comprise detecting lymphatic anomaly-associated SNVs, the lymphatic anomaly-associated SNV containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 μg of total RNA. Using Resonance Light Scattering (RLS) technology, as opposed to traditional fluorescence techniques, multiple reads can detect low quantities of mRNAs using biotin-labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus, any of the aforementioned techniques may be used to detect or quantify lymphatic anomaly-associated SNV marker expression and accordingly and to diagnose lymphatic anomalies or a risk of development thereof.

Treating Patients with Lymphatic Anomalies

The elucidation of the role played by lymphatic anomaly-associated SNVs described herein in modulating the lymphatic anomaly phenotype facilitates the repurposing of existing therapies, and the development of new therapies, useful for treatment of lymphatic anomalies. In some embodiments, the invention comprises administering one or more mTOR inhibitors, one or more PIK3K inhibitors, and/or one or more MEK inhibitors (e.g., one or more of the agents of Tables 1-2) to a patient having a lymphatic anomaly.

In some embodiments, the patient with a lymphatic anomaly to be treated has been diagnosed based on symptoms and a positive family history of lymphatic anomalies. In some embodiments, a variety of scanning technologies, such as plain film radiography, bone scanning, computed tomography, magnetic resonance imaging, and lymphoscintigraphy are used together with clinical presentation to diagnose a lymphatic anomaly. In some embodiments, a biopsy is performed to diagnose a lymphatic anomaly. In some embodiments, a lymphatic anomaly is diagnosed based on lymph vessel overgrowth. In some embodiments, a lymphatic anomaly is diagnosed based on abnormal formation of lymphatic vessels. In some embodiments, a lymphatic anomaly is diagnosed based on chylous effusions, including pericardial, pleural, or peritoneal effusions.

In some embodiments, the patient with a lymphatic anomaly to be treated has been diagnosed according to the diagnostic methods described herein.

In some embodiments, one or more mTOR inhibitors, one or more PIK3K inhibitors, and/or one or more MEK inhibitors (e.g., one or more of the agents of Tables 1-2) are useful in the preparation of a medicament to treat lymphatic anomalies. The one or more agent(s) may be formulated with a pharmaceutically acceptable excipient, carrier, buffer, stabilizer or other material well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, nasal, aerosolized, intramuscular, and intraperitoneal routes. In vitro systems or transgenic organisms comprising lymphatic anomaly-associated mutations may be used to select a particular agent for treatment of humans.

Agents useful for treatment include, but are not limited to, the agents of Tables 1 and 2. Some agents are listed on both Table 1 and 2, and the fact that they are not listed on both tables should be given no meaning.

TABLE 1

| | | |
|---|---|---|
| Rapamycin (Sirolimus) | Rapamycin (Sirolimus) is a specific mTOR inhibitor with IC50 of ~0.1 nM HEK293 cells. | Nat Genet, 2014, 46(4):364-70<br>Cancer Cell, 2011, 19(6):792-804<br>Cell Res, 2012, 22(6):1003-21 |
| Everolimus (RAD001) | Everolimus (RAD001) is an mTOR inhibitor of FKBP12 with IC50 of 1.6-2.4 nM in a cell-free assay. | Cell, 2012, 149(3):656-70<br>Nat Med, 2015, 10.1038/nm.3855<br>Cancer Cell, 2015, 27(4):533-46 |
| AZD8055 | AZD8055 is a novel ATP-competitive mTOR inhibitor with IC50 of 0.8 nM in MDA-MB-468 cells with excellent selectivity (~1,000-fold) against PI3K isoforms and ATM/DNA-PK. Phase 1. | Nat Med, 2015, 10.1038/nm.3855<br>Cancer Cell, 2015, 27(1):97-108<br>Cancer Cell, 2015, 27(4):533-46 |
| Temsirolimus (CCI-779, NSC 683864) | Temsirolimus (CCI-779, NSC 683864) is a specific mTOR inhibitor with IC50 of 1.76 μM in a cell-free assay. | Autophagy, 2011, 7(2):176-87<br>Cancer Res, 2014, 74(14):3947-58<br>Mol Oncol, 2014, 10.1016/j.molonc.2014.05.005 |
| KU-0063794 | KU-0063794 is a potent and highly specific dual-mTOR inhibitor of mTORC1 and mTORC2 with IC50 of ~10 nM in cell-free assays; no effect on PI3Ks. | Cell Stem Cell, 2012, 10(2):210-7<br>Circ Res, 2010, 107(10):1265-74<br>Oncogene, 2013, 10.1038/onc.2013.509 |
| MHY1485 | MHY1485 is a potent, and cell-permeable mTOR activator, and also potently inhibits autophagy. | |
| BEZ235 (NVP-BEZ235, Dactolisib) | BEZ235 (NVP-BEZ235, Dactolisib) is a dual ATP-competitive PI3K and mTOR inhibitor for p110α/γ/δ/β and mTOR(p70S6K) with IC50 of 4 nM/5 nM/7 nM/75 nM/6 nM in cell-free assays, respectively. Inhibits ATR with IC50 of 21 nM in 3T3$^{TopBP1-ER}$ cell. | Nature, 2012, 487(7408):505-9<br>Nat Med, 2015, 10.1038/nm.3855<br>Cancer Cell, 2012, 21(2):155-67 |
| PI-103 | PI-103 is a multi-targeted PI3K inhibitor for p110α/β/δ/γ with IC50 of 2 nM/3 nM/3 nM/15 nM in cell-free assays, less potent to mTOR/DNA-PK with IC50 of 30 nM/23 nM. | Cell, 2013, 153(4):840-54<br>Leukemia, 2013, 27(3):650-60<br>Leukemia, 2012, 26(5):927-33 |
| Torkinib (PP242) | Torkinib (PP242) is a selective mTOR inhibitor with IC50 of 8 nM in cell-free assays; targets both mTOR complexes with >10- and 100-fold selectivity for mTOR than PI3K6 or PI3Kα/β/γ, respectively. | J Clin Invest, 2015, 10.1172/JCI78018<br>Nat Chem Biol, 2013, 9(11):708-14<br>Autophagy, 2012, 8(6):903-14 |
| Tacrolimus (FK506) | Tacrolimus (FK506) is a 23-membered macrolide lactone, it reduces peptidyl-prolyl isomerase activity in T cells by binding to the immunophilin FKBP12 (FK506 binding protein) creating a new complex. | Biomed Pharmacother, 2013, 67(6):469-73<br>Universidad de Cantabria, 2012, Garcia Diaz<br>Biochim Biophys Acta, 2012, 1833(3):652-62 |
| Selumetinib (AZD6244) | Selumetinib (AZD6244) is a potent, highly selective MEK1 inhibitor with IC50 of 14 nM in cell-free assays, also inhibits ERK1/2 phosphorylation with IC50 of 10 nM, no inhibition to p38α, MKK6, EGFR, ErbB2, ERK2, B-Raf, etc. | Nature, 2012, 487(7408):505-9<br>Nature, 2010, 468(7326):968-72<br>Nature, 2016, 10.1038/nature19347 |
| PD0325901 | PD0325901 is a selective and non ATP-competitive MEK inhibitor with IC50 of 0.33 nM in cell-free assays, roughly 500-fold more potent than CI-1040 on phosphorylation of ERK1 and ERK2. Phase 2. | Nature, 2015, 10.1038/nature14413<br>Nature, 2015, 517(7534):391-5<br>Cell, 2015, 160(1-2):161-76 |
| Trametinib (GSK1120212) | Trametinib (GSK1120212) is a highly specific and potent MEK1/2 inhibitor with IC50 of 0.92 nM/1 8 nM in cell-free assays, no inhibition of the kinase activities of c-Raf, B-Raf, ERK1/2. | Nature, 2015, 517(7534):391-5<br>Nature, 2014, 510(7504):283-7<br>Nature, 2014, 508(7494):118-22 |

TABLE 1-continued

| | | |
|---|---|---|
| PD184352 (CI-1040) | PD184352 (CI-1040) is an ATP non-competitive MEK1/2 inhibitor with IC50 of 17 nM in cell-based assays, 100-fold more selective for MEK1/2 than MEK5. Phase 2. | Science, 2011, 331(6019):912-6 Nat Genet, 2011, 44(2):133-9 Cancer Cell, 2016, 10.1016/j.ccell.2016.01.006 |
| Pimasertib (AS-703026) | Pimasertib (AS-703026) is a highly selective, potent, ATP non-competitive allosteric inhibitor of MEK1/2 with IC50 of 5 nM-2 µM in MM cell lines. Phase 2. | Nat Commun, 2015, 6:6683 FASEB J, 2014, 10.1096/fj.13-247924 Oncotarget, 2016, 7(4):4265-78 |
| TAK-733 | TAK-733 is a potent and selective MEK allosteric site inhibitor for MEK1 with IC50 of 3.2 nM, inactive to Abl1, AKT3, c-RAF, CamK1, CDK2, c-Met, etc. | Nat Commun, 2016, 7:13701 Oncotarget, 2014, 5(20):9609-18 Mol Cancer Ther, 2014, 13(2):353-63 |
| AZD8330 | AZD8330 is a novel, selective, non-ATP competitive MEK 1/2 inhibitor with IC50 of 7 nM. | Cell, 2012, 32(34):4034-42 Oncotarget, 2016, 7(13):16273-81 |
| Binimetinib (MEK162, ARRY-162, ARRY-438162) | Binimetinib (MEK162, ARRY-162, ARRY-438162) is a potent inhibitor of MEK1/2 with IC50 of 12 nM in a cell-free assay. | Stem Cells, 2015, 10.1002/stem.1990 Mol Oncol, 2014, 8(3):544-54 Tumour Biol, 2015, 10.1007/s13277-015-3244-2 |
| SL-327 | SL327 is a selective inhibitor for MEK1/2 with IC50 of 0.18 µM/ 0.22 µM, no activity towards Erk1, MKK3, MKK4, c-JUN, PKC, PKA, or CamKII; capable of transport through the blood-brain barrier. | Psychopharmacology (Berl). 2011 Jul;216(1):63-73. |
| Refametinib (RDEA119, Bay 86-9766) | Refametinib (RDEA119, Bay 86-9766) is a potent, ATP non-competitive and highly selective inhibitor of MEK1 and MEK2 with IC50 of 19 nM and 47 nM, respectively. | J Neurosci, 2012, 32(14):4887-900 EBioMedicine, 2017, 15:90-99 Am J Cancer Res, 2016, 6(10):2235-2251 |
| Cobimetinib (GDC-0973, RG7420) | Cobimetinib (GDC-0973, RG7420) is a potent and highly selective MEK1 inhibitor with IC50 of 4.2 nM, showing more than 100-fold selectively for MEK1 over MEK2 and showed no significant inhibition when tested against a panel of more than 100 of serine-threonine and tyrosine kinases. | Cancer Discov, 2015, 10.1158/2159-8290.CD-15-0913 Mol Cell Proteomics, 2017, 16(2):265-277 Cancer Discov, 2016, 6(2):154-65 |

Table 2 provides agents that can be used alone, or in combination with any of the agents in Table 1 or in Table 2 to treat lymphatic anomalies.

TABLE 2

| Inhibitor Name | mTOR | mTORC1 | mTORC2 | Other Targets |
|---|---|---|---|---|
| BEZ235 (NVP-BEZ235, Dactolisib) | +++ | | | p110α, p110γ, p110δ |
| Rapamycin (Sirolimus) | ++++ | | | |
| Everolimus (RAD001) | +++ | | | |
| AZD8055 | ++++ | | | DNA-PK, PI3Kδ, PI3Kα |
| Temsirolimus (CCI-779, NSC 683864) | + | | | |
| PI-103 | + | | | p110α, p110δ, p110β |
| KU-0063794 | | ++ | ++ | |
| Torkinib (PP242) | ++ | | | p110δ, PDGFR, DNA-PK |
| Ridaforolimus (Deforolimus, MK-8669) | ++++ | | | |
| INK 128 (MLN0128) | ++++ | | | PI3Kα, PI3Kγ, PI3Kδ |
| Voxtalisib (SAR245409, XL765) | + | | | PI3Kγ, PI3Kα, PI3Kδ |
| Torin 1 | +++ | +++ | ++ | DNA-PK, p110γ, C2α |
| Omipalisib (GSK2126458, GSK458) | | ++++ | ++++ | p110α, p110δ, p110γ |
| OSI-027 | +++ | + | + | PI3Kγ, DNA-PK, PI3Kα |
| PF-04691502 | + | | | PI3Kδ, PI3Kα, PI3Kγ |
| Apitolisib (GDC-0980, RG7422) | + | | | p110α, p110δ, p110γ |
| GSK1059615 | ++ | | | PI3Kα, PI3Kβ, PI3Kδ |
| Gedatolisib (PF-05212384, PKI-587) | +++ | | | PI3Kα, PI3Kγ |
| WYE-354 | +++ | | | PI3Kα, PI3Kγ |
| AZD2014 | +++ | | | P-Akt (S473), pS6 (S235/236) |
| Torin 2 | ++++ | | | ATM, ATR, DNA-PK |

TABLE 2-continued

| Inhibitor Name | mTOR | mTORC1 | mTORC2 | Other Targets |
|---|---|---|---|---|
| WYE-125132 (WYE-132) | ++++ | | | |
| PP121 | ++ | | | PDGFR, Hck, VEGFR |
| WYE-687 | ++ | | | PI3Kα, PI3Kγ, p38α |
| CH5132799 | + | | | PI3Kα, PI3Kγ, PI3Kβ |
| WAY-600 | ++ | | | PI3Kα, PI3Kγ |
| ETP-46464 | ++++ | | | ATR, DNA-PK, PI3Kα |
| GDC-0349 | +++ | | | PI3Kα |
| XL388 | ++ | ++ | + | CYP2C9, CYP3A4 |
| Zotarolimus (ABT-578) | +++ | | | |
| Tacrolimus (FK506) | √ | | | |
| BGT226 (NVP-BGT226) | √ | | | PI3Kα, PI3Kγ, PI3Kβ |
| Palomid 529 (P529) | | √ | | |
| Chrysophanic Acid | √ | | | EGFR |
| TAK-733 | | | | MEK |
| PD-325901 | | | | MEK |
| Selumetinib | | | | MEK |
| Binimetinib (MEK162) | | | | MEK |
| Cobimetinib (XL518) | | | | MEK |
| Trametinib (GSK1120212 | | | | MEK |
| Pimasertib (AS-70326) | | | | MEK |
| Trametinib | | | | MEK |
| PD184352 | | | | MEK |
| SL-327 | | | | MEK |
| AZD8330 | | | | MEK |

In order to treat an individual having a lymphatic anomaly, or to alleviate a sign or symptom of the disease, suitable agents targeting the genes disclosed herein can be administered in combination in order to provide therapeutic benefit to the patient. Such agents should be administered in an effective dose.

Once the genetic alteration(s) is/are identified, therapy is then devised to modulate biological and signaling pathways affected by the altered gene. For example, mTOR inhibitors can be used alone or in combination with additional mTOR inhibitors. Similarly, PIK3K inhibitors can be used alone, or in combination with any of the PIK3K inhibitors listed above. In cases where it is desirable to inhibit the MAPK (MEK1/MEK2) and ERK pathways, MEK inhibitors can used alone or in combination with other MEK/ERK inhibitors. In certain embodiments, treatment entails administration of an mTOR inhibitor together with PIK3K inhibitor. In other embodiments, mTOR and MEK/ERK inhibitors are combined to provide therapeutic benefit to the patient. In another approach, PIK3K and MEK/ERK inhibitor are combined to ameliorate symptoms of disease. For the specific ARAF gain of function mutation described herein, an effective therapy comprises administration of a MEK/ERK inhibitor. The combinatorial therapies described above can act in an additive fashion. In other embodiments, the combined agents act synergistically to alleviate symptoms.

First, a biological sample, and/or genotyping information may be obtained from a patient. Genetic information gleaned from nucleic acids present in the sample would then be assessed for the presence or absence of the lymphatic anomaly-associated SNV for example. The presence of these mutations indicating the presence of a lymphatic anomaly risk or disease, along with the simultaneous identification of the genes affected, provides the clinician with guidance as to which therapeutic agents are appropriate. The total treatment dose or doses (when two or more targets are to be modulated) can be administered to a subject as a single dose or can be administered using a fractionated treatment protocol, in which multiple/separate doses are administered over a more prolonged period of time, for example, over the period of a day to allow administration of a daily dosage or over a longer period of time to administer a dose over a desired period of time. One skilled in the art would know that the amount of lymphatic anomaly agent required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having a lymphatic anomaly.

The effective dose of lymphatic anomaly therapeutic agent(s) will depend on the mode of administration, and the weight of the individual being treated. The dosages described herein are generally those for an average adult but can be adjusted for the treatment of children. The dose will generally range from about 0.001 mg to about 1000 mg.

In an individual suffering from a lymphatic anomaly in particular, a more severe form of the disease, administration of lymphatic anomaly therapeutic agents can be particularly useful when administered in combination, for example, with a conventional agent for treating such a disease. The skilled artisan would administer lymphatic anomaly therapeutic agent(s), alone or in combination and would monitor the effectiveness of such treatment using routine methods such as pulmonary, bowel, thyroid, or inflammatory function determination, radiologicor immunologic assays, or, where indicated, histopathologic methods. Other agents for the treatment of lymphatic anomaly include systemic chemotherapy, interferon alfa therapy, radiotherapy, or surgery, to alleviate the symptoms underlying the disease.

Administration of the pharmaceutical preparation is preferably in an "effective amount" this being sufficient to show benefit to the individual. This amount prevents, alleviates, abates, or otherwise reduces the severity of lymphatic anomaly symptoms in a patient. Treatment of patients having lymphatic anomaly with an efficacious amount of an mTOR inhibitor, a PIK3K inhibitor, and/or a MEK inhibitor (e.g., an agent from Tables 1-2) may produce improvements in lymph structure, decreased chylous pleural effusions, improved respiratory function, tapering of concomitant medication usage, or increased survival.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

Pharmaceutical compositions that are useful in the methods of the invention may be administered systemically in parenteral, oral solid and liquid formulations, subcutaneously, intradermally, intramuscularly, sublingually, topically, auricularly (OTIC), buccally, conjunctivally, cutaneously, dentally, via electro-osmosis, endo-cervically, via the sinus or trachea, enteral, epidurally, via infiltration, interstitially, intra-abdominally, intra-arterially, intra-articular, intra-biliary, intra-bronchially, intra-bursal, intra-cardiac, intra-cartilaginous, intra-caudal, intracavernous, intracavitary, intracerebral, intradermal, intra-lymphatic, intrapericardially, intraperitoneal, nasally, percutaneous, respiratory, ophthalmic, suppository, aerosol, topical or other known routes of administration. In addition to the agent(s) useful for treating a lymphatic anomaly, the pharmaceutical compositions may contain pharmaceutically-acceptable carriers and other ingredients known to enhance and facilitate drug administration. Thus, such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to deliver/administer the appropriate agent to a patient according to the methods of the invention. The use of nanoparticles to deliver such agents, as well as cell membrane permeable peptide carriers that can be used are described in Crombez et al., Biochemical Society Transactions v35:p44 (2007).

Administration of agent(s) useful for treating a lymphatic anomaly may be done following successfully detecting or quantifying lymphatic anomaly-associated SNV marker expression and accordingly, diagnosing a lymphatic anomaly or a risk of development thereof. Detecting or quantifying lymphatic anomaly-associated SNV marker expression may guide the selection of the specific agent used for treatment. Detecting or quantifying lymphatic anomaly-associated SNV marker expression may indicate that a particular treatment is not appropriate for a given subject.

In other embodiments, treatment for a lymphatic anomaly may be done based on clinical diagnosis of disease and treatment may be initiated in the absence of detecting or quantifying genetic sequence information. In other embodiments, treatment for a lymphatic anomaly may be done based on clinical diagnosis of disease and treatment may be initiated in the absence of detecting or quantifying lymphatic anomaly-associated SNV marker expression.

In other embodiments, treatment for a lymphatic anomaly may be done based on clinical diagnosis of disease and treatment may be initiated when lymphatic anomaly-associated SNV marker expression is not different from controls.

In some embodiments, treatment is administered in patients who do not have an SNV in EPHB4, PIK3R4, PIK3R6, mTOR, or ARAF.

In some embodiments, two or more agents from Tables 1-2 are administered. In some embodiments, three or more agents from Tables 1-2 are administered.

In some embodiments, the agent(s) that are administered have a profile of inhibition of mTOR, mTORC1, and mTORC2. The activity of mTOR, mTORC1, and mTORC2 may be termed "mTOR signaling." Inhibition of mTOR, mTORC1, and mTORC2 may be referred to as inhibition of mTOR signaling. In some embodiments, this agent(s) with a profile of inhibition of mTOR, mTORC1, or mTORC2 is not included in Tables 1-2, but has an in vitro or cell-free profile of inhibition of mTOR, mTORC1, or mTORC2. In some embodiments, the inhibitor of mTOR signaling, mTOR inhibitor, mTORC1 inhibitor, or mTORC2 inhibitor has an IC50 of less than 100M, less than 10 µM, less than 1 µM, less than 100 nM, less than 10 nM, or less than 1 nM.

In some embodiments, the agent(s) is selective for inhibition of mTOR, mTORC1, and/or mTORC2 over other targets. In some embodiments, the agent(s) is not selective for inhibition of mTOR, mTORC1, and/or mTORC2 over other targets. In some embodiments, the agent(s) inhibit mTOR, mTORC1, and/or mTORC2 and also have other measurable biologic effects.

In some embodiments, the agent(s) is an ATP-competitive mTOR inhibitor. In some embodiments, the agent(s) is a mTOR inhibitor that is not ATP-competitive. In some embodiments, the agent is a dual mTORC1/C2 inhibitor.

In some embodiments, the agent(s) is an inhibitor of phosphoinositide 3-kinase (PI3K). In some embodiments, the agent(s) is an inhibitor of PI3K and mTOR, mTORC1, or mTORC2. In some embodiments, the agent(s) is an inhibitor of PI3K without inhibition of mTOR, mTORC1, or mTORC2. In some embodiments, the PI3K inhibitor has an IC50 of less than 100 µM, less than 10 µM, less than 1 µM, less than 100 nM, less than 10 nM, or less than 1 nM.

In some embodiments, the agent(s) is an inhibitor of peptidyl-prolyl cis-trans isomerase, the gene product of FKB12. In some embodiments, the agent is an inhibitor of FK506 binding. In some embodiments, the agent(s) is an inhibitor of peptidyl-prolyl cis-trans isomerase or the gene product of FKB12 and mTOR, mTORC1, or mTORC2. In some embodiments, the agent(s) is an inhibitor of peptidyl-prolyl cis-trans isomerase or the gene product of FKB12 without inhibition of mTOR, mTORC1, or mTORC2. In some embodiments, the inhibitor of peptidyl-prolyl cis-trans isomerase or the gene product of FKB12 has an IC50 of less than 100 µM, less than 10 µM, less than 1 µM, less than 100 nM, less than 10 nM, or less than 1 nM.

In some embodiments, the agent(s) is an inhibitor of DNA-activated protein kinase (DNA-PK). In some embodiments, the agent(s) is an inhibitor of DNA-PK and mTOR, mTORC1, or mTORC2. In some embodiments, the agent(s) is an inhibitor of DNA-PK without inhibition of mTOR, mTORC1, or mTORC2. In some embodiments, the inhibitor of DNA-PK has an IC50 of less than 100 µM, less than 10 µM, less than 1 µM, less than 100 nM, less than 10 nM, or less than 1 nM.

In some embodiments, the agent(s) is an inhibitor of phosphatidylinositol-4,5-bisphosphate 3-kinase, also known as p110. In some embodiments, the agent(s) is an inhibitor of one or more subunits of p110 ($\alpha$, $\beta$, $\gamma$, $\delta$, etc.). In some embodiments, the agent(s) is an inhibitor of p110 and mTOR, mTORC1, or mTORC2. In some embodiments, the agent(s) is an inhibitor of p110 without inhibition of mTOR, mTORC1, or mTORC2. In some embodiments, the inhibitor of p110 has an IC50 of less than 100 µM, less than 10 µM, less than 1 µM, less than 100 nM, less than 10 nM, or less than 1 nM.

In some embodiments, the agent(s) is an inhibitor of P70S6 kinase (P70S6K). In some embodiments, the agent(s) is an inhibitor of P70S6K and mTOR, mTORC1, or mTORC2. In some embodiments, the agent(s) is an inhibitor of P70S6K without inhibition of mTOR, mTORC1, or mTORC2. In some embodiments, the inhibitor of P70S6K has an IC50 of less than 100 µM, less than 10 µM, less than 1 µM, less than 100 nM, less than 10 nM, or less than 1 nM.

In some embodiments, the inhibitor is an MEK1/2 inhibitor which inhibits the mitogen-activated protein kinase enzymes MEK1 and/or MEK2. They can be used to affect the MAPK/ERK pathway which is often overactive in some cancers and other disorders.

In some embodiments, the agent(s) is rapamycin or BEZ-235 (dactolisib). Rapamycin, an mTOR inhibitor, is also known as sirolimus. BEZ-235, also known as dactolisib or NVP-BEZ235, is a compound with known activity against p110, PI3K, and mTOR.

In some embodiments, the agent to be administered in the treatment methods is selected from Rapamycin (Sirolimus), Everolimus (RAD001), AZD8055, Temsirolimus (CCI-779, NSC 683864), KU-0063794, MHY1485, BEZ235 (NVP-BEZ235, Dactolisib), PI-103, Torkinib (PP242), Tacrolimus (FK506), Ridaforolimus (Deforolimus, MK-8669), INK 128 (MLN0128), Voxtalisib (SAR245409, XL765), Torin 1, Omipalisib (GSK2126458, GSK458), OSI-027, PF-04691502, Apitolisib (GDC-0980, RG7422), GSK1059615, Gedatolisib (PF-05212384, PKI-587), WYE-354, AZD2014, Torin 2, WYE-125132 (WYE-132), PP121, WYE-687, CH5132799, WAY-600, ETP-46464, GDC-0349, XL388, Zotarolimus (ABT-578), Tacrolimus (FK506), BGT226 (NVP-BGT226), Palomid 529 (P529), and Chrysophanic Acid.

In some embodiments, the agent to be administered is an MEK inhibitor selected from Selumetinib (AZD6244). PD0325901, Trametinib (GSK120212), PD184352 (CI-1040), Pimasertib (AS-703026), TAK-733, AZD8330, Binimetinib (MEK162, ARRY-162, ARRY-438162), SL-327, Refametinib (RDEA119, Bay 86-9766), and Cobimetinib (GDC-0973, RG7420).

Combinations of the agents described above should have efficacy for the treatment of lymphatic anomalies. The combinations below can act additively or synergistically to treat LAM. In certain embodiments, the combinations for administration are selected from 1) Ridaforolimus and Trametinib; 2) Ridaforolimus and Selumetinib or Cobimetinib; 3) BEZ235 and Selumetinib; 4) Omipalisib and Selumetinib or Trametinib; 5) Everolimus and Trametinib or Selumetinib; 6) Sirolimus, Ridaforolimus and Selumetinib; 7) Sirolimus, Ridaforolimus and Trametinib; 8) Torkinib and Trametinib; 9) BEZ235, Torkinib and Trametinib; and 10) Sirolimus and Gedatolisib and Trametinib.

In some embodiments, treatment with an agent(s) listed herein is used in combination with one or more of systemic chemotherapy, interferon alfa, radiotherapy, and/or surgery.

Methods of Identifying Useful Therapeutic Reagents

Since the SNVs identified herein have been associated with the etiology of lymphatic anomaly, methods for identifying agents that modulate the activity of the genes and their encoded products containing such SNVs should result in the generation of efficacious therapeutic agents for the treatment of this condition.

The chromosomal regions described herein contain protein coding regions which provide suitable targets for the rational design of therapeutic agents which modulate their activity. Small peptide molecules corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the SNV-containing nucleic acids based on conformation or key amino acid residues required for function. A combinatorial chemistry approach will be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

A further technique for drug screening involves the use of host eukaryotic cell lines, cells (such as endothelial cells) or whole animal models (e.g., transgenic mice or zebrafish) which have a nonfunctional or altered lymphatic anomaly-associated gene. In some cases, the transgenic organism comprises cells that have mutation of c.2334+1G>C in EPHB4; c.3481A>G:p.S1161G in PIK3R4; c.1393-7C>T in PIK3R6; c.6818A>G:p.P2273L in mTOR; or and c.640T>C:p.S214P in ARAF. These host cell lines, cells or transgenic animals are defective at the polypeptide level. The host cell lines or cells are grown in the presence of drug compound. For example, in a zebra fish model, the rescue of caudal and or D/V vessel structure can be assessed. Additionally, induction of phosphorylation by mTOR in a host cell line may be assessed.

An example method of drug screening would be a method for identifying an agent that alters cellular signaling, such as an agent listed in Tables 1-2. This method would comprise providing cells expressing at least one nucleic acid comprising at least one lymphatic anomaly-associated SNV; providing cells which express the cognate wild type sequences corresponding to the lymphatic anomaly-associated SNV; contacting the cells expressing at least one lymphatic anomaly-associated SNV and cells expressing the cognate wild type sequence with a test agent; and analyzing whether said agent alters cellular signaling.

Host cells expressing the lymphatic anomaly-associated SNVs of the present invention or functional fragments thereof provide a system in which to screen potential compounds or agents for the ability to modulate the development of lymphatic anomalies. Thus, in one embodiment, the nucleic acid molecules of the invention may be used to create recombinant cell lines for use in assays to identify agents which modulate aspects of aberrant mTOR signaling associated with lymphatic anomalies and aberrant vessel formation. Also provided herein are methods to screen for compounds capable of modulating the function of proteins encoded by SNV-containing nucleic acids.

Another approach entails the use of phage display libraries engineered to express fragment of the polypeptides encoded by the SNV containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

In another embodiment, the availability of lymphatic anomaly-associated altered nucleic acids enables the production of strains of laboratory mice carrying the altered nucleic acids of the invention. These lymphatic anomaly-associated altered nucleic acids may be c.2334+1G>C in EPHB4; c.3481A>G:p.S1161G in PIK3R4; c.1393-7C>T in PIK3R6; c.6818A>G:p.P2273L in mTOR; and/or c.640T>C:p.S214P in ARAF. Transgenic mice expressing the lymphatic anomaly-associated mutations of the invention provide a model system in which to examine the role of the protein encoded by the mutated nucleic acid in the development and progression towards lymphatic anomalies. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various processes associated with the lymphatic anomaly phenotypes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of altered lymphatic anomaly-associated nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

One type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated, mutation-containing lymphatic anomaly-associated genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{+6}$ and $10^{-3}$. Non-homologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabino-fluranosyl)-5-iodou-racil, (FIAU). By this counter selection, the number of homologous recombinants in the surviving transformants can be increased. Utilizing mutated lymphatic anomaly-associated nucleic acid as a targeted insertional cassette provides means to detect a successful insertion as visualized, for example, by acquisition of immunoreactivity to an antibody immunologically specific for the polypeptide encoded by EPHB4 nucleic acid and, therefore, facilitates screening/selection of ES cells with the desired genotype.

As used herein, a knock-in animal is one in which the endogenous murine gene, for example, has been replaced with human lymphatic anomaly-associated gene of the invention. Such knock-in animals provide an ideal model system for studying the development of lymphatic anomalies.

As used herein, the expression of a mutated lymphatic anomaly-associated nucleic acid, fragment thereof, or a lymphatic anomaly-associated fusion protein can be targeted in a "tissue specific manner" or "cell type specific manner" using a vector in which nucleic acid sequences encoding all or a portion of lymphatic anomaly-associated nucleic acid are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein. Alternatively, the transgene may be under the control of an inducible promoter which may function in a tissue specific or "whole body" manner.

The nucleic acid sequence encoding the lymphatic anomaly-associated mutant of the invention may be operably linked to a variety of different promoter sequences for expression in transgenic animals. Such promoters include, but are not limited to a prion gene promoter such as a hamster or mouse Thy-1 promoter; a PGK promoter; or a CMV promoter for the expression of transgenes in desired cell types.

Methods of use for the transgenic mice of the invention are also provided herein. Transgenic mice into which a nucleic acid containing the mutated lymphatic anomaly-associated nucleic acid or its encoded protein have been introduced are useful, for example, to develop screening methods to screen therapeutic agents to identify those capable of modulating the development of lymphatic anomalies.

Detection Products and Kits

Compositions or products that are useful in detecting lymphatic anomaly SNVs are encompassed. For example, lymphatic anomaly-associated SNV-containing nucleic acids, vectors expressing the same, lymphatic anomaly-associated SNV-containing marker proteins and anti-lymphatic anomaly-specific marker antibodies are products capable of detecting SNVs c.2334+1G>C in EPHB4, c.3481A>G:p.S1161G in PIK3R4, c.1393-7C>T in PIK3R6, c.6818A>G:p.P2273L in mTOR, or c.640T>C:p.S214P in ARAF. Nucleic acid probes having sufficient length and characteristics to detect SNVs c.2334+1G>C in EPHB4, c.3481A>G:p.S1161G in PIK3R4, c.1393-7C>T in PIK3R6, c.6818A>G:p.P2273L in mTOR, or c.640T>C:p.S214P in ARAF are also encompassed. Detection products may be labeled such that they can be detected.

Any products useful in detecting the lymphatic-anomaly-associated SNVs can be incorporated into a kit. Any products useful in treating lymphatic anomalies can be incorporated into a kit. Kits containing such detection and therapeutic products are encompassed. The kit may contain one or more of a lymphatic anomaly-associated SNV specific marker polynucleotide or one or a collection of such markers immobilized on a solid support, gene chip, an oligonucleotide, a polypeptide, a peptide, an antibody, a label, a marker, a reporter, a pharmaceutically acceptable carrier, a physiologically acceptable carrier, instructions for use, a container, a vessel for administration, an assay substrate, or any combination thereof.

The following examples are provided to illustrate certain embodiments of the invention. They are not intended to limit the invention in any way.

Example I

To identify the genetic basis of LAM/GLA, whole exome sequencing (ES) was performed on DNA samples obtained from family members from three generations of a family comprising six individuals affected with heterogeneous forms of lymphatic anomalies. Affected family members presented with different lymphatic anomalies, including significant venous stasis in combination with lymphatic disease. The pedigree demonstrated an autosomal dominant inheritance model, as shown in FIG. 1.

The proband in family 1 is a 24-year-old man with a lifelong history of complex lymphatic disease manifesting primarily as a right-sided chylous effusion. The diagnosis of pulmonary lymphangiomatosis was previously confirmed by histopathological evidence on an open lung biopsy at 4 months of age. A lymphangiogram evidenced no normal lymphatic valves. Retrograde flow of lymph was found, which included suspicion of flow into (rather than out of) lungs. There was a proliferation of lymphatic channels in the retroperitoneum around the spine and in the lungs. Lymphatic channels were dysfunctional and the flow was abnormal after injection of lymph nodes with gadolinium. There was T2 enhancement of the peribronchial tree bilaterally, suggestive of swelling and lymphatic channels surrounding the airways, the peribronchial lymphatics. Evidence of fibrosis at the right lung base, where there had previously been a chylothorax, was also found. His family history is notable for lymphatic defects in his mother, maternal uncle and aunts, as well as maternal grandfather. All affected family members have venous changes, although there is a variable degree of lymphatic involvement in some family members.

Exomic sequencing was performed on the proband (i.e., affected individuals) and healthy sister, both parents, unaffected maternal aunt, as well as affected maternal grandfather, who provided the most effective baseline data. All missense, nonsense, splice-altering, and coding indel mutations were examined that matched the autosomal dominant inheritance model of the family. Results were filtered to exclude synonymous variants, variants with minor allele frequency (MAF) greater than 0.5%, and variants previously identified in controls by our in-house exome variant database. Relevant candidates were taken forward for manual curation.

As a result, a single base pair substitution, c.2334+1G>C, was identified that results in a splice site mutation within the EPHB4 gene as the causal mutation. Co-segregation of the mutation with phenotype was confirmed by Sanger sequencing, which demonstrated the presence of the heterozygous splicing variant in the six affected individuals and absence of the mutation in seven unaffected family members. A single asterix in FIG. 1 indicates an individual who tested positive for this causal mutation, while a double asterix indicates an individual who tested negative for the mutation.

EPHB4 is expressed on valves in lymphatic-collecting vessels, and the affected individuals in the proband have lymphangiography demonstrating retrograde flow suggestive of absent or dysfunctional valves. The c.2334+1G>C mutation was absent from the 1000 Genomes Project, COSMIC, ESP6500SI and ExAC 61,000 exomes v0.3 release. RNA-seq with skin biopsies obtained from the lead proband demonstrated that the EPHB4 splice-altering mutation creates a cryptic splice donor that causes the retention of the intervening 12 bp of the intron and leads to nonframeshift 4 amino acids insertion in the highly conserved catalytic loop of protein kinase domain, which was also confirmed by standard Sanger sequencing (data not shown). RT-PCR confirmed two bands in EBV transformed lymphoblastoid cell lines (LCLs) generated from the proband and mother and showed skin from unaffected controls had higher expression level for wild type of EPHB4 (data not shown). Protein immunoblot for EPHB4 in healthy family members and patient-derived LCLs showed a band of predicted size (120 kD) in all samples, with a more prominent band in controls (date not shown).

Figure 2:
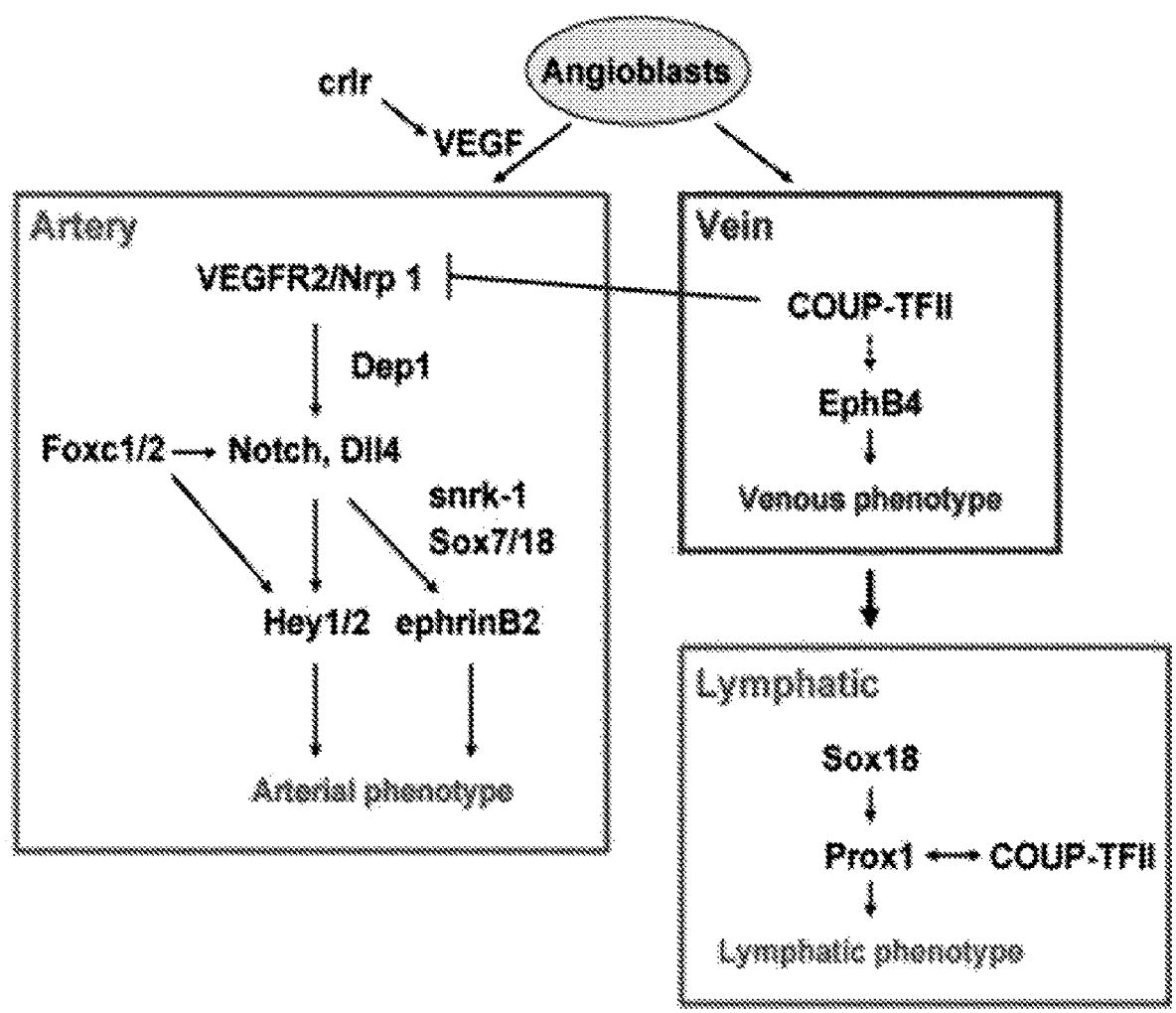
FIG. 2. A schematic diagram of the role played by EPHB4 in vessel development.

EPHB4 encodes for Ephrin B-type receptor 4, which is a receptor tyrosine kinase and recognizes Ephrin B2 (EFNB2) as a specific ligand. The EFNB2/EPHB4 pathway has previously been shown to impact venous and lymphatic cell fate determination. FIG. 2 provides a schematic overview of signaling pathways that give rise to the arterial phenotype, the venous phenotype and the lymphatic phenotype, and highlights the role of EPHB4 in development of the venous phenotype.

Example II

Ten additional families were sequenced leading to identification of 3 additional disease-causing genes. The first was a missense mutation in phosphoinositide-3-kinase regulatory subunit 4 (PIK3R4), the second was a homozygous splicing mutation in phosphoinositide-3-Kinase Regulatory Subunit 6 (PIK3R6), and a third was a missense mutation in mTOR. PIK3R4, PIK3R6, MTOR, and EPHB4a are related in that they converge on the same physiological PI3K/AKT/mTOR pathway. Thus, this pathway provides an ideal target for therapeutics that may have efficacy for the treatment of lymphatic anomalies.

Table 3 provides a summary of these data. The family with the mutation described above in EPHB4 at c.2334+1G>C was designated as family-1. For family-2, exonic sequencing revealed a homozygous variant, c. 1393-7C>T, in PIK3R6 in the proband with both parents being heterozygous. PIK3R6 encodes the regulatory subunit (p84) that pairs with the catalytic subunit p110 to form a Class IB PI3K complex. For families 3 and 4, a very rare missense mutation, c.6818A>G:p.P2273L, in MTOR, and a novel missense mutation, c.3481A>G:p.S1161G, in PIR3R4, respectively were identified. In families 5 and 6, a recurrent ARAF mutation, c.640T>C:p.S214P, in the conserved phosphorylation site was identified, which putatively would result in a gain of function because the phosphorylation of residue S214 is responsible for regulation of the A-RAF proto-oncogene (ARAF). Inheritance mode was characterized as autosomal dominant (AD) or autosomal recessive (AR), as noted in Table 3.

TABLE 3

Summary data on patients with complex lymphatic anomalies and associated mutations

| Participants | Gene | Mutation | Inheritance Mode | Diagnosis | Pleural effusion |
|---|---|---|---|---|---|
| Family-1 | EPHB4 | c.2334+1G>C | AD | GLA and venous stasis | Yes |
| Family-2 | PIK3R6 | c.1393–7C>T | AR | GLA | Yes |
| Family-3 | MTOR | c.6818A>G:p.P2273L | AD | Primarily Abdominal Lymphatic Anomaly | Limited |
| Family-4 | PIK3R4 | c.3481A>G:p.S1161G | AD | GLA | Yes |
| Family-5 | ARAF | c.640T>C:p.S214P | AD | Lymphangiectasia | Yes |
| Family-6 | ARAF | c.640T>C:p.S214P | AD | Lymphangiectasia | Yes |

Example III

In vivo zebrafish studies of the four identified human mutations confirmed that they were relevant in lymphatic anomalies.

To determine if the c.2334+1G>C mutation in EPHB4 affects the catalytic activity of the gene product, expression constructs containing the wild type and mutant versions of EPHB4 were generated. A plasmid containing the EPHB4 coding sequence was obtained from GE Dharmacon (cat # MHS6278-202833446, Lafayette, Colo.). The discovered 12 base pair insertion was made via the Quikchange II mutagenesis kit (Agilent, Santa Clara, Calif.) using primers SEQ ID NO: 1 and SEQ ID NO: 2. The coding sequence was amplified by PCR using forward primer SEQ ID NO: 3 and reverse primer SEQ ID NO: 4 and ligated into the EcoRI and NotI sites of pBabe+CMV Puro. A FLAG tag was inserted into the coding sequence following the signal peptide via the Q5 Mutagenesis kit (NEB, Ipswich, Mass.) using the forward primer SEQ ID NO: 5 and the reverse primer SEQ ID NO: 6. All sequences were confirmed by Sanger sequencing.

HEK239T cells and the A375 melanoma cell line were obtained from ATCC (Manassas, Va.). Transfections were performed using Fugene HD (Promega, Madison, Wis.), with 3 µg DNA and 9 µl of the transfection reagent, according to manufacturer's protocols. For stimulation of transfected cells with Ephrin-B2-Fc, 6-well plates (not tissue culture treated, Thermo Scientific) were coated overnight at 37° C. with either Ephrin-B2-Fc (cat #7397-EB, R&D Systems) or IgG1, kappa from human myeloma plasma (cat #15154, Sigma) at 5 µg/mL in 50 mM sodium carbonate solution (pH 9.6). The plates were washed with PBS, blocked with 1% BSA in PBS for 30 minutes at 4° C., and washed again with PBS. Transfected cells were removed from their plates using 10 mM EDTA in DMEM, washed and resuspended in serum free DMEM, and added to coated plates. Plates were placed at 4° C. for 15 minutes and moved to 37° C. for 20 minutes, after which cells were lysed. Where indicated, FLAG immunoprecipitations (IPs) were performed using Anti-FLAG M2 Affinity Gel (cat # A2220, Sigma, St. Louis, Mo.). IPs and lysates were run on NuPAGE 4-12% Bis-Tris gels and blotted with anti-phosphotyrosine—4G10-Biotin (cat #16-103, EMD Millipore, Billerica Mass.) and anti-EPHB4 (cat # AF3038, R&D Systems, Minneapolis, Minn.).

Figure 3A:
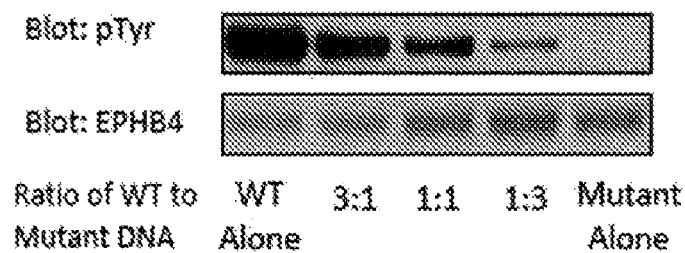
FIGS. 3A and 3B. EPHB4 mutation leads to inactive EPHB4 kinase.
Figure 3B:
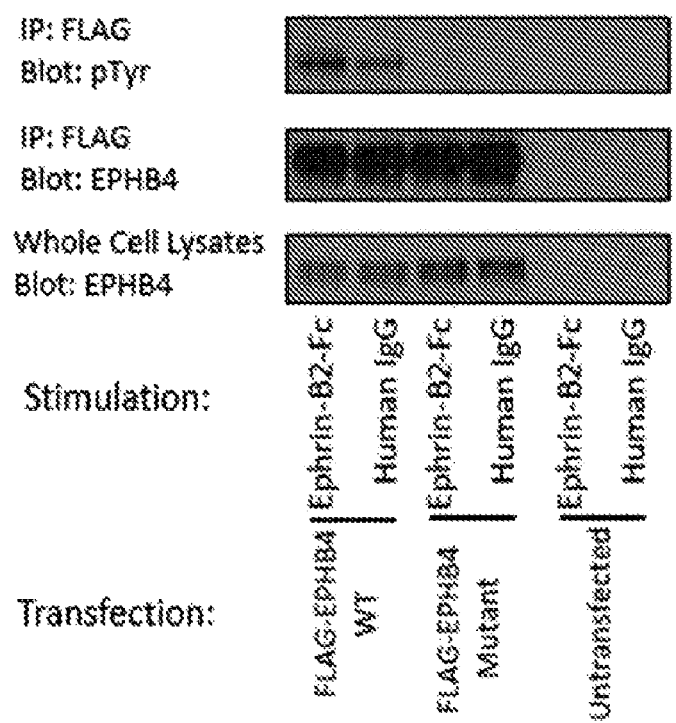

Transfection of wild type EPHB4 into 293T cells resulted in constitutive tyrosine phosphorylation of the protein (FIG. 3A, phosphorylated Tyr (pTyr) in top panel and total EPHB4 in lower panel). In contrast, dramatically less tyrosine phosphorylation was detected with transfection of the mutant. As previously described for a different mutation of EPHB4 in hydrops fetalis, transfection of mixtures of the wild type and mutant proteins resulted in reduced phosphorylation, roughly in proportion to the amount of the mutant protein transfected. See Martin-Almedina S, et al. J Clin Invest 126:3080-3088 (2016). Transfection of mutant EPHB4 into the A375 melanoma cell line (FIG. 3B) resulted in far less constitutive phosphorylation compared with transfection of wild type EPHB4 (comparing signal with pTyr blot versus EPHB4 following FLAG immunoprecipitation or whole cell lysates). Stimulation of the transfected cells with Ephrin-B2, the ligand for EPHB4, resulted in induction of phosphorylation of the wild type EPHB4, but not the mutant EPHB4 (data not shown). These results suggest that the 4-amino acid insertion caused by the splice-altering mutation severely impacts the kinase activity of the mutant EPHB4 and that the presence of the mutant can affect the phosphorylation of the wild type protein.

Figure 4:
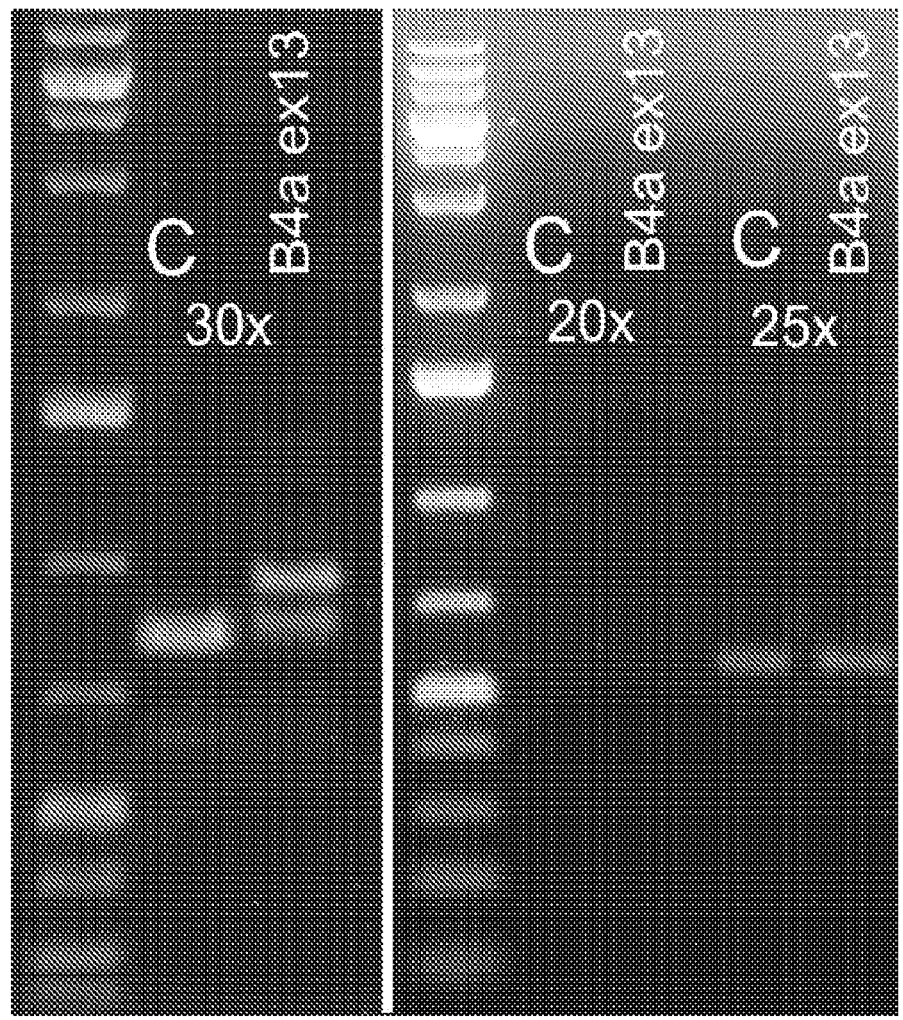
FIG. 4. A gel showing cDNA knock down of EPHB4 in zebrafish using exon 13 morpholino at 2 dpf (days post-fertilization) at different loading concentrations. Exon 13 has 216 base pairs. C=control (no morpholino).

To evaluate the functional consequences of the EPHB4 variant, an mRNA knock down approach was taken using morpholino antisense oligonucleotides in zebrafish that inhibit the same splice junction of exon 13 as identified in the patients by using tg(fli1:GFP) line. The morpholino sequence targeting exon 13 was CGAGAGCAGTATTTACCAGTGAGCT (SEQ ID NO: 15) and was used at a concentration of 0.8 mM. For pik3r6 ex4 del the concentration used was 0.25 mM and for pik3r6 ex13 del, the concentration was 0.5 mM. RT-PCR analysis showed efficient knockdown by ~66% (FIG. 4).

Figure 5E:
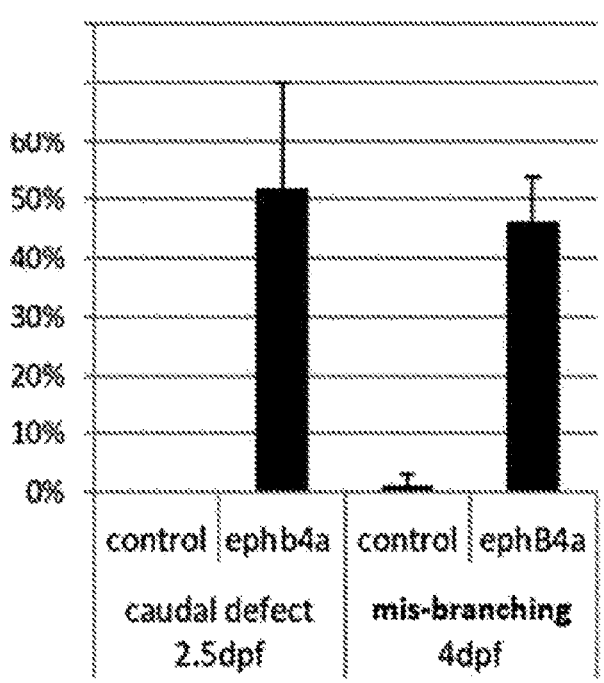

A fusion of vessels and a general expansion in the caudal vascular plexus at 2.5 days post-fertilization (dpf) (comparing control in FIG. 5A to morpholino treated in FIG. 5B), which was quantified in FIG. 5E (labeled as "caudal defect"), was observed in approximately 52% of the morpholino injected larvae (4 experiments with 225 animals, P<0.0006). Furthermore, lateral aberrant and excess branching of the intersomitic vessels at 4 days post-fertilization (dpf) was observed in approximately 46% of the injected larvae (FIG. 5C [control] and FIG. 5D [morpholino treated]). FIG. 5E shows quantification (labeled as "misbranching", 6 experiments, 259 animals, P<3.9E-08). The morphology and lateral branching shows that these aberrant branches have lymphatic character. Amplification of ephb4a cDNA derived from the Morphants (MOs) revealed that specifically targeting the 13th exon resulted in aberrant splicing with either a small or larger insertion. Sanger sequencing showed that the smaller band was a 30 bp in-frame insertion (encoding VNTALVLSIL), while the larger band was due to the retention of the intron between exon 13 and 14 presumably resulting in a premature stop codon.

To validate the morpholino data, a mutant line carrying a point mutation ephb4a$^{sa11431}$ originally discovered by the Sanger Institute with the tilling approach (see Kettleborough R N, et al., Nature 496:494-497 (2013)) was acquired. However, an in-cross of mutant carriers with the tg(fli1: GFP) background did not show a defect in the caudal plexus or mis-branching of intersomitic vessels. Potentially, a second ephb4 gene in zebrafish, ephb4b, could compensate for the complete absence of ephb4a. Indeed, injection of an ephb4b morpholino targeting the exon 13 splice junction, resulted in fusion and expansion of the caudal plexus at 54 hours post-fertilization (hpf). At higher concentrations around 70% of these larvae also developed mis-branching on 4 dpf (data not shown). Importantly, these phenotypes were not induced when morpholino only targets ephb4b in wild type larvae (data not shown).

Figure 5F:
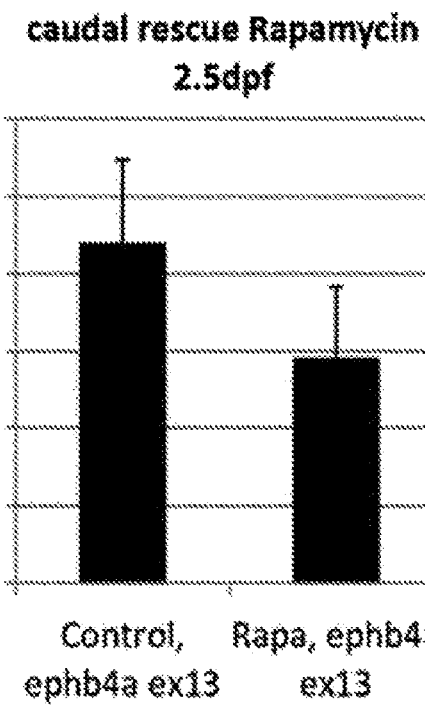
Figure 5G:
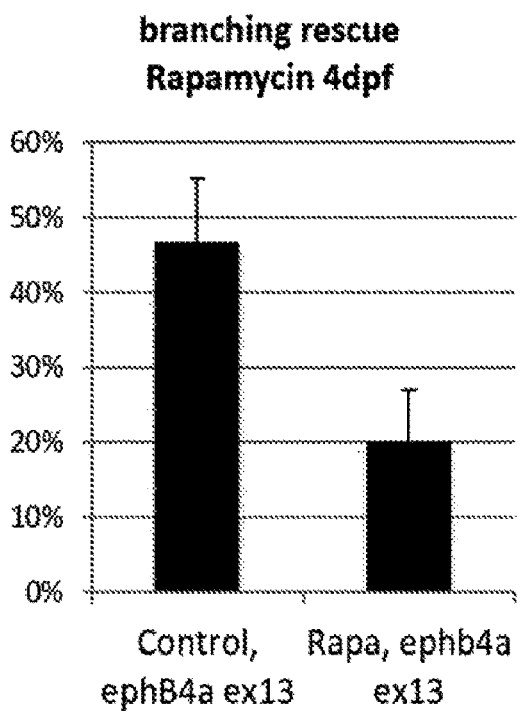
Figure 5H:
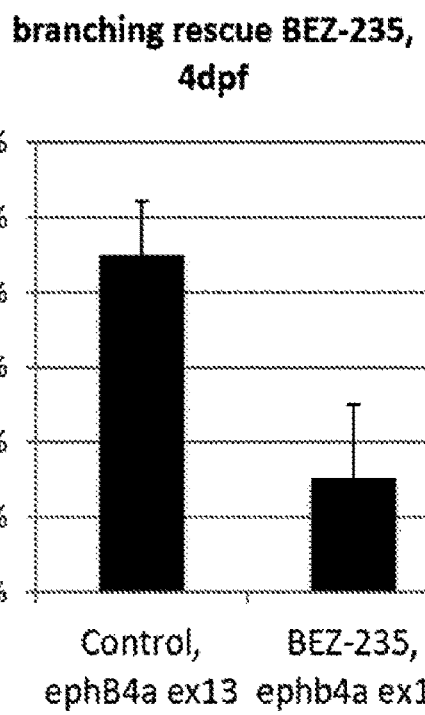

It has been suggested that mTORC1 is an important signaling pathway for lymphatic development (see Sun et al., Nature 496:494-497 (2015)). Thus, zebrafish exposed to morpholino antisense oligonucleotides to inhibit the same splice junction of exon 13 of EPHB4 were treated with mTORC1 inhibitors rapamycin (1 µM) and BEZ-235 (100 nM). Treatment with rapamycin from 24 hpf to 56 hpf showed a significant rescue of the defects in the caudal vascular plexus from 44% (control, without treatment) to 29% (6 experiments, 321 animals, P<0.01), as shown in FIG. 5F. Rapamycin also rescued the intersomitic vessel misbranching when treating from 2.5 dpf to 4 dpf (47% [control, without treatment] vs. 20%) (FIG. 5G, 6 experiments, 136 animals, P<0.00007). BEZ-235 also rescued the mis-branching from 45% (control) to 15% (FIG. 5H, 2 experiments, 41 animals, P<0.037).

Thus, data from zebrafish confirmed the role of EPHB4 in proper development of the lymphatic system. These data support that a mutation in EPHB4, such as c.2334+1G>C predicts the lymphatic anomaly phenotype as seen in the pedigree of human patients.

Next, two morpholino strains against pik3r6 were developed, both targeting a splice donor site with one on exon 4 and the other on exon 13, covering the same ortholog region as was identified in the patient. None of these morpholinos induced a phenotype at the caudal vascular plexus, but both caused severe mis-branching of the intersomitic vessels. Deletions of exon 4 (FIG. 6B) cause a more severe phenotype than deletion of exon 13. (FIGS. 6A-D, ex 4: 55% of morpholino injected, 7 experiments, 210 animals, P<1.13E-07; ex13: 47%, 3 experiments, 70 animals P<0.0016).

Figure 6A:
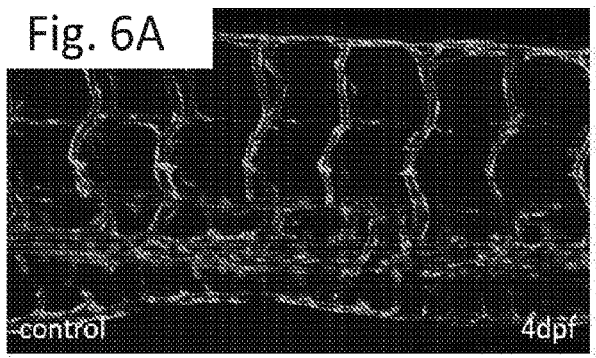
FIGS. 6A-6F. pik3r6 knock-down induces mTOR signaling dependent mis-branching intersomitic vessels.
Figure 6B:
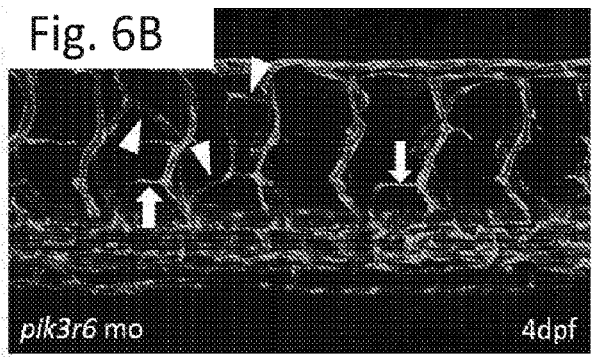
Figure 6C:
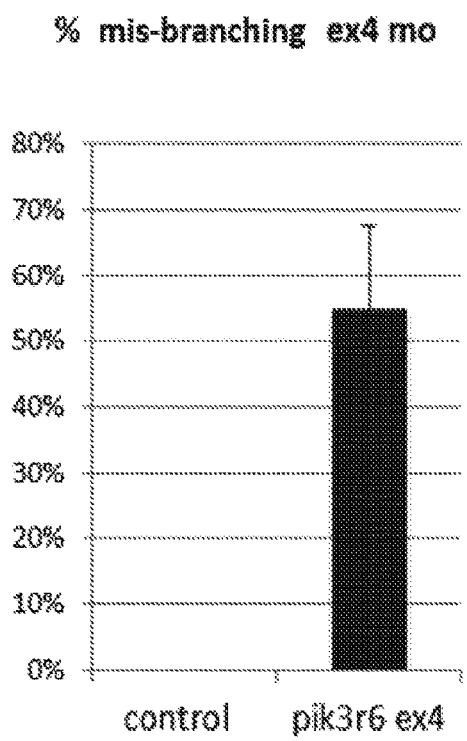
Figure 6D:
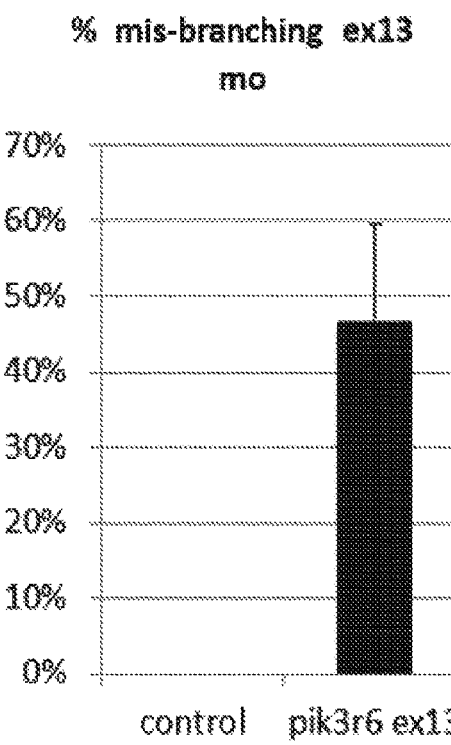
Figure 6E:
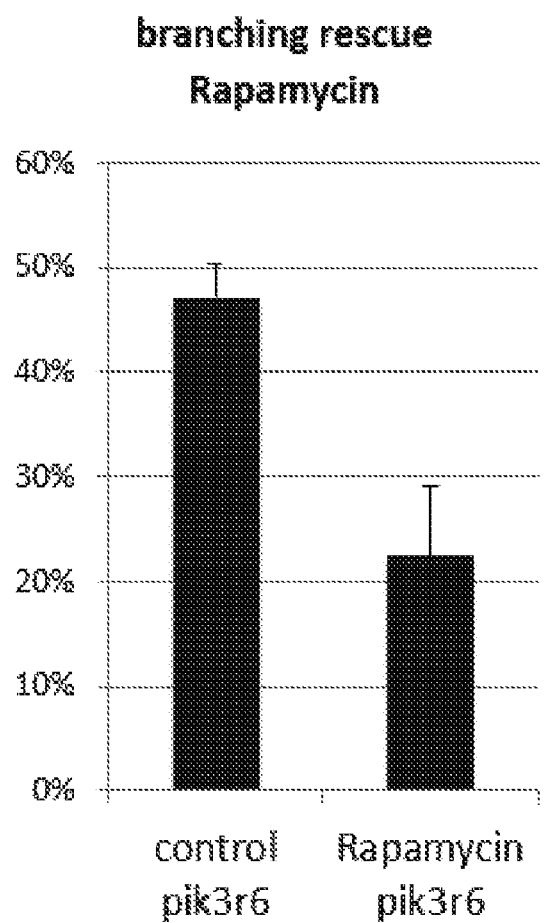
Figure 6F:
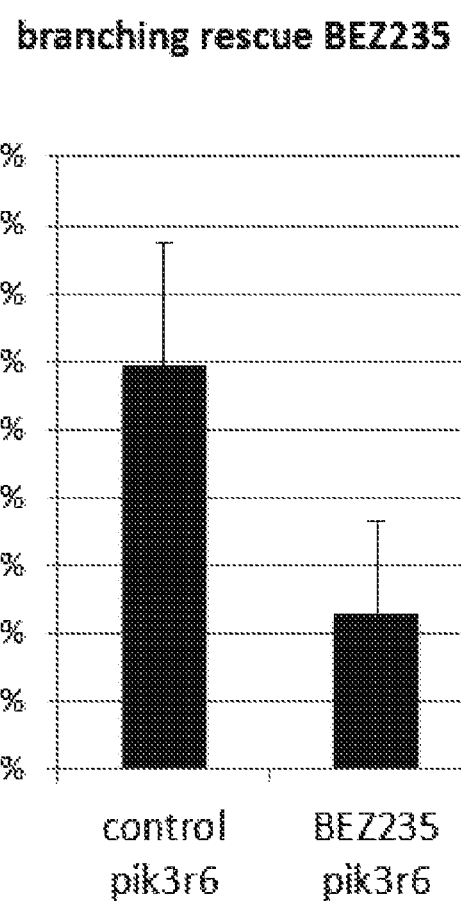

Further, it was examined if rapamycin and BEZ-235 could also inhibit the mis-branching phenotype induced by the pik3r6 exon 4 morpholino. Indeed, both drugs showed they could reverse the functional process resulting in vascular normalization. Rapamycin reduced the number of animals with aberrant branches from 47% to 21% (FIG. 6E, 4 experiments, 190 animals, P<0.003) BEZ-235 reduced mis-branching animals from 56% to 23% (FIG. 6F, 4 experiments, 103 animals, P<0.008).

To investigate if pik3r4 has an influence on lymphatic development in zebrafish, a morpholino was designed against the splice junction site of exon 3. The morpholino induced mis-branching in 16% of injected larvae that either affected intersomitic blood vessels or lymphatic vessels (evaluated by morphology and position of the vessel) compared to control that had 5% mis-branching (FIGS. 7A-7D; 2 experiments; 198 animals; P<0.05).

To determine the biochemical effects caused by the PIK3R6 and EPHB4 morpholinos, multiple zebrafish larvae were lysed between 4.5 and 5 dpf, and the lysates were analyzed for mTORC1 signaling by Western blots. Trunk sections of zebrafish larvae 4.5-5 dpf were lysed in radio-immunoprecipitation assay (RIPA) buffer supplemented with protease inhibitors (Complete protease inhibitor cocktail tablets, Roche, Mannheim, Germany). Approximately 5 micrograms of protein were separated on NuPAGE 4-12% Bis-Tris gels run with MOPS SDS running buffer (Life Technologies, Carlsbad, Calif.). Western blotting was performed using the following antibodies: p-p70 S6 Kinase T389 (cat #9205S, Cell Signaling, Danvers, Mass.), Phospho-mTOR Ser2448 (cat #5536P, Cell Signaling), HIF1 (cat # LS-C287203, LSBio, Seattle, Wash.), beta-actin (cat # AC-15, Santa Cruz Biotechnology, Santa Cruz, Calif.).

Both PIK3R6 (FIG. 8A) and EPHB4 MOs (FIG. 8B) showed activated mTORC1 signaling as detected by phosphorylation of both mTOR and its downstream target p70S6K. The activation of mTORC1 by either morpholino was inhibited by treatment of the developing larvae with rapamycin. Activation by the PIK3R6 morpholino was also inhibited by BEZ235, a dual PI-3-kinase and mTOR inhibitor. Further, a cellular model for the EPHB4 mutation was developed using CRISPR. The exon 12 to 14 region of EPHB4 cDNA was amplified by PCR and directly sequenced to confirm the knock-in. The pSpCas9(BB)-2A-Puro vector containing the specific target sequence for EPHB4 locus (gRNA-EPHB4) was co-transfected with a single-stranded donor oligonucleotides (ssODN) into 293T cells using the Lipofectamine 2000 transfection reagent per manufacturer's instructions. ssODN contains a single base mismatch to the genomic sequence to recreate the EPHB4 mutation and 4 or 3 synonymous or non-coding changes respectively. pSpCas9(BB)-2A-Puro (PX459) V2.0 was purchased from Addgene (Plasmid ID #62988). The guide RNAs (gRNAs) used in this study (SEQ ID NO:7 for EPHB4) is present immediately upstream of a Protospacer Adjacent Motif (PAM) and were designed using the gRNA designer from MIT (http://crispr.mit.edu/). For gRNAs assembly, a pair of synthesized oligos for each targeting site with the following sequence (hEPHB4-F=SEQ ID NO: 8, hEPHB4-R=SEQ ID NO: 9, hPIK3R6-F=SEQ ID NO: 10, hPIK3R6-R=SEQ ID NO: 11) were annealed and pasted in pSpCas9(BB)-2A-Puro using BbsI (NEB, Ipswich, Mass.) restriction enzyme site. The synthesized ssODNs (180 bases, SEQ ID NO.: 12) were purchased from IDT.

Figure 9:
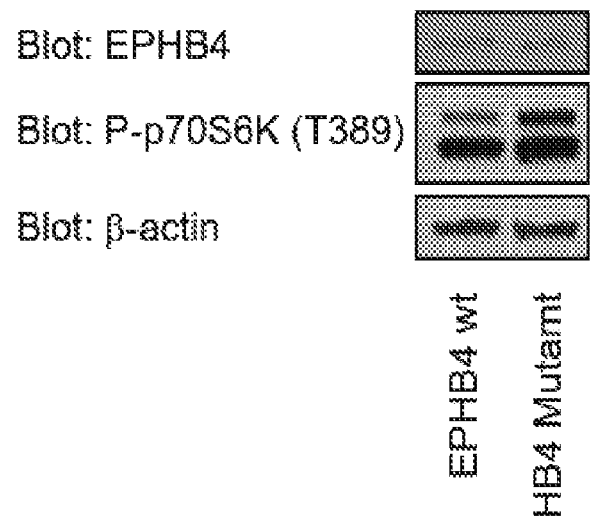
FIG. 9. Western blotting analysis of the wild-type HEK293T cells or EPHB4 mutant cells by gene-editing. Cells containing the EPHB4 splice-altering mutation displayed higher P-p70S6K levels than wild type cells. Blotting for beta-actin was used as a loading control.

Following transfection of the CRISPR reagents, western blot analysis of the gene-edited cells with the EPHB4 splice-altering mutation displayed higher phosphorylation of p70S6K (P-p70S6K) levels as compared with that of wild type cells (FIG. 9).

Expression of mTOR was also found to be significantly increased in HeLa cells transfected with wild-type or mutated mTOR cDNAs. A mammalian expression vector (pcDNA3-FLAG mTOR wt) containing the human wild-type mTOR cDNA with a FLAG tag at the N-terminal (ID #26603) was obtained from Addgene. This expression vector carrying the wild-type mTOR cDNA was used to generate P2273L mTOR mutant with a Q5 Site-Directed Mutagenesis Kit (NEB, Ipswich, Mass.) according to the instructions of the manufacturer. The primers were designed using a template specific mutagenic primer design program. The primer sequences were SEQ ID NO: 13 and SEQ ID NO: 14.

HeLa cells were obtained from American Type Culture Collection (ATCC) and grown at 37° C. in Dulbecco's modified Eagle's medium (DMEM) supplemented with 10% fetal bovine serum (FBS). HeLa cells were transiently transfected with an empty vector (e.v.), wild-type (wt) or P2273L mutant mTOR expression vectors using the Lipofectamine 2000 transfection reagent per manufacturer's instructions (Invitrogen Life Technologies, CA). Medium was changed 24 h after transfection. 36-48 hr after transfection, cells were washed twice with ice-cold Phosphate-buffered saline (PBS) and lysed on ice using a freshly prepared ice-cold cell lysis buffer containing 50 mM Tris-HCl, pH 7.4, 100 mM NaCl, 50 mM β-glycerophosphate, 10% glycerol (w/v), 1% NP-40 (w/v), 1 mM EDTA, 2 mM NaVO4, and a complete, EDTA-free protein inhibitor cocktail (Roche Applied Science, Mannheim Germany) at 20 µl per mL of lysis buffer. Cell lysates were collected in a 1.5 mL microfuge tube disrupted by vortex and incubated on ice for 5 min. Cell lysates were then centrifuged at 12,000 rpm for 5 min at 4° C. The supernatants were collected and protein concentrations were measured using a Bradford protein assay kit (Bio-Rad Laboratories, Hercules Calif.). This cell lysate was used for Western blotting. Western blotting was performed using 10-30 µg of cell lysates resolved on SDS/PAGE and transferred to a PVDF membrane (Millipore Co., Bedford, Mass.). The membrane was blocked with 5% skim milk/TBS containing 0.1% Tween 20 (TBST) for 1 hour at room temperature and the membrane was then sliced based on the molecular weights. Membranes were incubated 1 h at room temperature (RT) or overnight at 4° C. with primary antibodies, including anti-EPHB4, anti-phospho-p70S6K (Cat #9234, Cell Signaling Technology, Danvers, Mass.), anti-FLAG (Cat #2972, Cell Signaling Technology, Danvers Mass.), or anti-β-actin (Cat # sc-1616R, Santa Cruz Biotechnology) antibodies. After washing four times with TBST, blots were incubated with respective HRP-conjugated anti-rabbit or anti-mouse secondary antibodies (Cat # sc-2004 and # c-2005, Santa Cruz Biotechnology) for 1 hour at RT. After washing with TBST, protein bands on the membrane were detected with enhancement chemiluminescence (ECL) reaction reagents (Thermo Scientific, Waltham, Mass.) and exposed to X-ray films.

Figure 10:
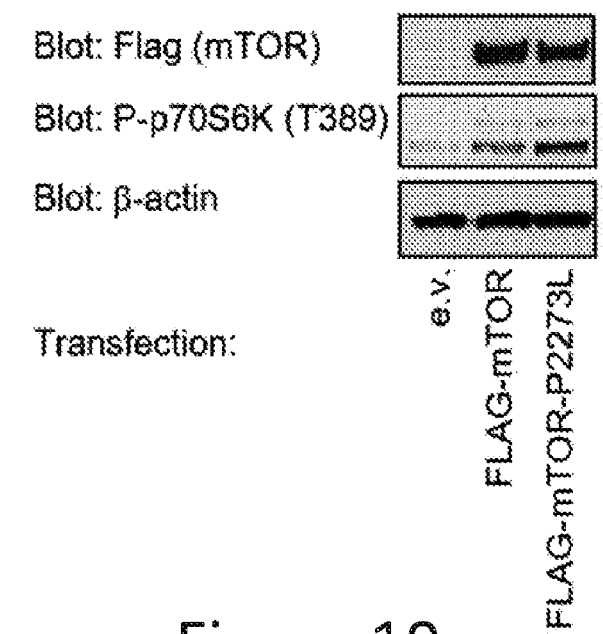
FIG. 10. mTOR P2273L mutant shows increased protein kinase activity. Western blotting analysis of the HeLa cells transfected with flag-tagged vector, wild-type mTOR and P2273L-mTOR mutant. Activation is reflected by increased phosphorylation of p70S6K. e.v.=empty vector. Blotting for beta-actin was used as a loading control.

The mTOR mutant, P2273L, resulted in increased phosphorylation of p70S6K (P-p70S6K), as compared with wild-type mTOR or empty vector (e.v.) (FIG. 10), indicative of an enhanced signaling and consistent with a gain-of-function mutation.

Experiments to evaluate the ARAF c.640T>C:p.S214P mutation have been performed as described in Example II. Endothelial cells expressing human ARAF wild type or S214P mutant were generated and incubated with increasing doses of ERK inhibitor (1-100 nm) in 5% FBS media. Using these cells lines, it was determined that ARAF S214P mutation impairs angiogenesis and decreases migration abilities of endothelial cells (See FIGS. 11A and 12).

Figure 11G:
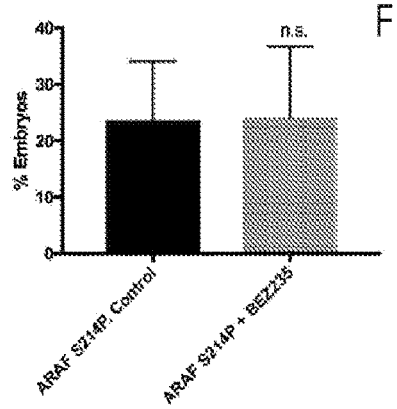
Figure 11H:
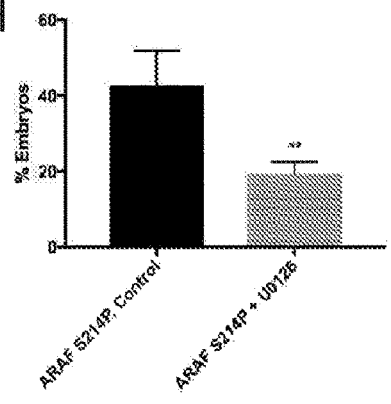
Figure 11I:
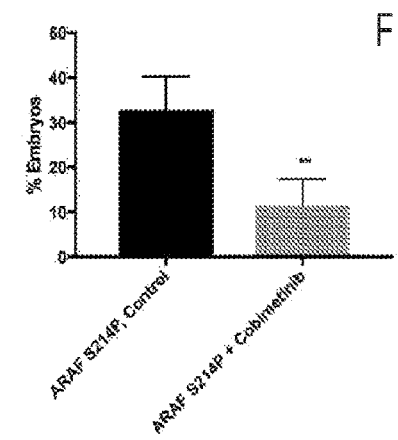
Figure 11J:
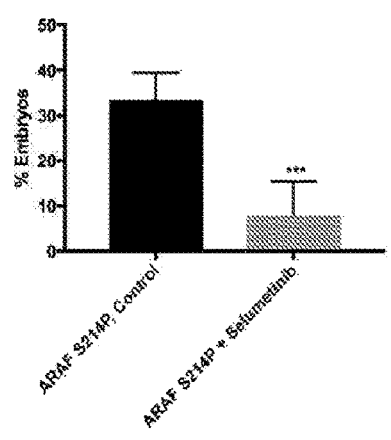
Figure 11K:
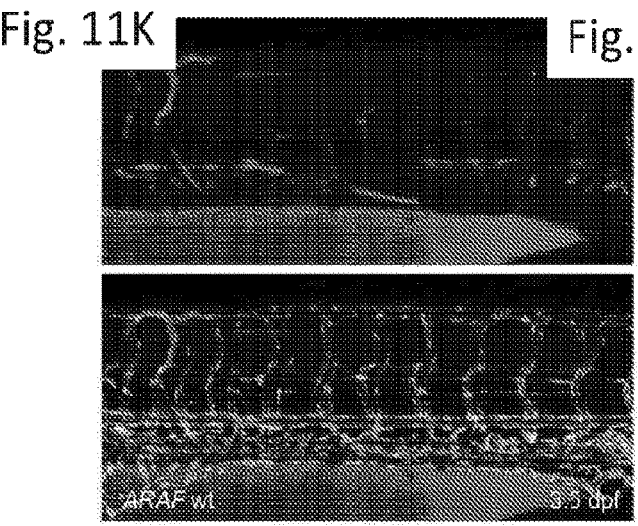
Figure 11L:
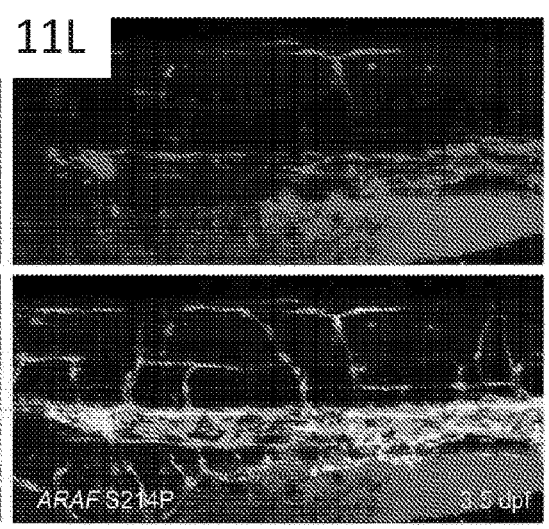
Figure 12:
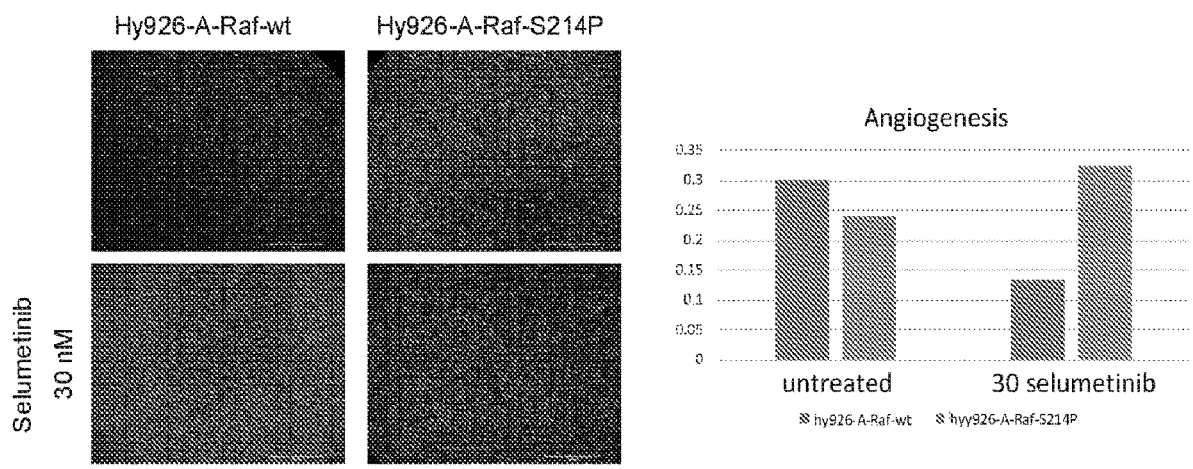
FIG. 12. LGA-associated mutation A-RafS214P impaired migratory properties of endothelial cells. Cell migration was determined using Millipore Transwell chambers. Hy926 cells expressing A-Raf wt or A-Raf-S214P (300 µl, $2\times10^5$ cells/ml) were seeded in the upper chambers of Transwell plates and 400 µl of DMEM with 10% FBS was added to the lower chambers. The plates were then placed in an incubator at 37° C. with 5% $CO_2$ for 24 hours. After incubation, the cells remaining in the upper chamber were carefully removed, and the Transwell membrane was fixed with 4% PFA and stained with 0.5% crystal violet. The amount of crystal violet was determined by Optical Density after treatment with 1% SDS solution. The data suggest that selumetinib may partially restore angiogenesis.

Transgenic mosaic expression of human ARAF wild type or S214P mutant in zebrafish was investigated (11B-L). Expression of human ARAF induced enlarged caudal vessels and the enlarged caudal vessels defect was detected in 21% of transgenic expression of human ARAF S214P, but not wild type at 2 dpf (*** P<0.001) (FIG. 11C-E). A partial rescue is detected in tube formation and migration after treatment with MEK inhibitors (e.g., U0126, cobimetinib, 1-10 µM in physiologic sea water, and selumetinib 50-100 µM in physiologic sea water). See FIGS. 11F-L and 12. Endothelial cells expressing EPHB4 wild type, EPHB4-Dex13 mutant, or EPHB4-12 bp insertion mutant were also generated. The Ephb4 mutations did not appear to impair tube formation of these cell lines (data not shown).

Example IV

Treatment of a Patient with ARAF Mutation with ERK Inhibitor:

A 12 year old male with severe GLA who had required multiple surgeries to drain and cauterize his chest was found to have the above described ARAF mutation. He had previously been treated with Rapamycin for six months with no effects and continued to have progressive chylus requiring surgery. He subsequently required multiple chest surgeries and was running out of options when the ARAF mutation was identified and therapy with a ERK inhibitor was authorized. Subsequently, he was started on Trametinib (the only MEK inhibitor approved in children and with comparable effects to those of selumetinib and cobimetinib), 1 mg daily and followed monthly for response. His lung function test, which showed severe restrictive lung diseases before, improved overall by 45% (FVC, FEV1) after one month therapy with Trametinib was begun. He had no side effects from the Trametinib therapy except possibly some dry skin around his wrists. He also was feeling well, was less winded, and was eating better following Trametinib treatment. Following treatment, he was able to climb a flight of stairs without stopping and shoot hoops outside, neither of which he could do before. Following therapy, his pulse oxygen was normal with the lowest being recorded in the morning (95%) and he went without use of oxygen. His CT chest scan was essentially unchanged following two months on therapy suggesting his disease had not progressed (pulmonary function tests are much more sensitive in measuring response to therapy than are radiographic measures). Taken together, this is evidence that Trametinib halted GLA disease progression, (e.g., improved lung function and oxygen saturation, and alleviated requirements for supplemental oxygen), suggesting that ERK inhibitor therapy may be beneficial for patients with GLA and ARAF mutations and potentially for patients with mutations that affect ERK function.

Thus, the data presented in this application identify a novel splice-altering mutation in EPHB4 that was identified for the first time in six patients with complex lymphatic anomalies, including GLA and venous stasis, and resulted in increased mTORC1 activity. This c.2334+1G>C mutation in EPHB4 leads to non-frameshift insertion in the protein kinase domain, which participates in phosphorylation in forward signaling.

Functional data both validate the pathogenicity of the c.2334+1G>C in mutation EPHB4 and show the insertion decreases the phosphorylation state of EPHB4 protein. Modeling the splicing-altering EPHB4 mutation in zebrafish resulted in vessel mis-branching and deformities in the lymphatic vessel development, indicative of possibly differentiation defects both in blood and lymphatic vessels and mimicking the presentations of the patients in Family-1. Strikingly, drugs that inhibit mTOR signaling were able to rescue this mis-branching phenotype.

Additionally, multiple germline mutations in PIK3R6, MTOR and PIK3R4 that converge on PI3K/mTOR pathway and functional data support the ability of these mutations to cause caudal defects and mis-branching in zebrafish. Thus, the supportive evidence presented here is highly suggestive that mutations in PIK3R6, MTOR and PIK3R4 also play non-redundant roles in lymphangiogenesis process.

A recurrent ARAF mutation was also found in the conserved phosphorylation site with presumable gain-of-function effect. ARAF activation in turn upregulates ring finger and FYVE-like domain containing E3 ubiquitin protein ligase (RFFL), leading to polyubiquitylation and destabilization of proline rich 5 like (PRR5L), a component of mTORC2 and suppressor of protein kinase C (PKC) phosphorylation, to achieve persistent PKC activation which leads to cell pro-growth and pro-migration. Thus, there is also mechanistic basis for mutation in ARAF having a causative role in development of lymphatic anomalies. Notably, treatment of a patient harboring a mutation in ARAF with an ERK inhibitor successfully ameliorated symptoms of disease.

REFERENCES

1. Alitalo K, Tammela T, Petrova T V 2005 Lymphangiogenesis in development and human disease. Nature 438: 946-953
2. Trenor C C, 3rd, Chaudry G 2014 Complex lymphatic anomalies. Semin Pediatr Surg 23:186-190
3. Levine C 1989 Primary disorders of the lymphatic vessels—a unified concept. J Pediatr Surg 24:233-240
4. Wassef M, Blei F, Adams D, Alomari A, Baselga E, Berenstein A, Burrows P, Frieden I J, Garzon M C, Lopez-Gutierrez J C, Lord D J, Mitchel S, Powell J, Prendiville J, Vikkula M 2015 Vascular Anomalies Classification: Recommendations From the International Society for the Study of Vascular Anomalies. Pediatrics 136: e203-214
5. Hilliard R I, McKendry J B, Phillips M J 1990 Congenital abnormalities of the lymphatic system: a new clinical classification. Pediatrics 86:988-994
6. Smeltzer D M, Stickler G B, Fleming R E 1986 Primary lymphatic dysplasia in children: chylothorax, chylous ascites, and generalized lymphatic dysplasia. Eur J Pediatr 145:286-292
7. Faul J L, Berry G J, Colby T V, Ruoss S J, Walter M B, Rosen G D, Raffin T A 2000 Thoracic lymphangiomas, lymphangiectasis, lymphangiomatosis, and lymphatic dysplasia syndrome. Am J Respir Crit Care Med 161: 1037-1046
8. Brouillard P, Boon L, Vikkula M 2014 Genetics of lymphatic anomalies. J Clin Invest 124:898-904
9. Luks V L, Kamitaki N, Vivero M P, Uller W, Rab R, Bovee J V, Rialon K L, Guevara C J, Alomari A I, Greene A K, Fishman S J, Kozakewich H P, Maclellan R A, Mulliken J B, Rahbar R, Spencer S A, Trenor C C, 3rd, Upton J, Zurakowski D, Perkins J A, Kirsh A, Bennett J T, Dobyns W B, Kurek K C, Warman M L, McCarroll S A, Murillo R 2015 Lymphatic and other vascular malformative/overgrowth disorders are caused by somatic mutations in PIK3CA. J Pediatr 166:1048-1054 e1041-1045
10. Kurek K C, Luks V L, Ayturk U M, Alomari A I, Fishman S J, Spencer S A, Mulliken J B, Bowen M E, Yamamoto G L, Kozakewich H P, Warman M L 2012 Somatic mosaic activating mutations in PIK3CA cause CLOVES syndrome. Am J Hum Genet 90:1108-1115
11. Lindhurst M J, Sapp J C, Teer J K, Johnston J J, Finn E M, Peters K, Turner J, Cannons J L, Bick D, Blakemore L, Blumhorst C, Brockmann K, Calder P, Cherman N, Deardorff M A, Everman D B, Golas G, Greenstein R M, Kato B M, Keppler-Noreuil K M, Kuznetsov S A, Miyamoto R T, Newman K, Ng D, O'Brien K, Rothenberg S, Schwartzentruber D J, Singhal V, Tirabosco R, Upton J, Wientroub S, Zackai E H, Hoag K, Whitewood-Neal T, Robey P G, Schwartzberg P L, Darling T N, Tosi L L, Mullikin J C, Biesecker L G 2011 A mosaic activating mutation in AKT1 associated with the Proteus syndrome. N Engl J Med 365:611-619
12. Revencu N, Boon L M, Mendola A, Cordisco M R, Dubois J, Clapuyt P, Hammer F, Amor D J, Irvine A D, Baselga E, Dompmartin A, Syed S, Martin-Santiago A, Ades L, Collins F, Smith J, Sandaradura S, Barrio V R, Burrows P E, Blei F, Cozzolino M, Brunetti-Pierri N, Vicente A, Abramowicz M, Desir J, Vilain C, Chung W K, Wilson A, Gardiner C A, Dwight Y, Lord D J, Fishman L, Cytrynbaum C, Chamlin S, Ghali F, Gilaberte Y, Joss S, Boente Mdel C, Leaute-Labreze C, Delrue M A, Bayliss S, Martorell L, Gonzalez-Ensenat M A, Mazereeuw-Hautier J, O'Donnell B, Bessis D, Pyeritz R E, Salhi A, Tan O T, Wargon O, Mulliken J B, Vikkula M 2013 RASA1 mutations and associated phenotypes in 68 families with capillary malformation-arteriovenous malformation. Hum Mutat 34:1632-1641
13. Burrows P E, Gonzalez-Garay M L, Rasmussen J C, Aldrich M B, Guilliod R, Maus E A, Fife C E, Kwon S, Lapinski P E, King P D, Sevick-Muraca E M 2013 Lymphatic abnormalities are associated with RASA1 gene mutations in mouse and man. Proc Natl Acad Sci USA 110:8621-8626
14. Lo I F, Brewer C, Shannon N, Shorto J, Tang B, Black G, Soo M T, Ng D K, Lam S T, Kerr B 2008 Severe neonatal manifestations of Costello syndrome. J Med Genet 45:167-171
15. Fabretto A, Kutsche K, Harmsen M B, Demarini S, Gasparini P, Fertz M C, Zenker M 2010 Two cases of Noonan syndrome with severe respiratory and gastroenteral involvement and the SOS1 mutation F623I. Eur J Med Genet 53:322-324
16. Joyce S, Gordon K, Brice G, Ostergaard P, Nagaraja R, Short J, Moore S, Mortimer P, Mansour S 2016 The lymphatic phenotype in Noonan and Cardiofaciocutaneous syndrome. Eur J Hum Genet 24:690-696
17. Morcaldi G, Bellini T, Rossi C, Maghnie M, Boccardo F, Bonioli E, Bellini C 2015 Lymphodysplasia and Kras Mutation: A Case Report and Literature Review. Lymphology 48:121-127
18. Makinen T, Adams R H, Bailey J, Lu Q, Ziemiecki A, Alitalo K, Klein R, Wilkinson G A 2005 PDZ interaction site in ephrinB2 is required for the remodeling of lymphatic vasculature. Genes Dev 19:397-410
19. Kume T 2010 Specification of arterial, venous, and lymphatic endothelial cells during embryonic development. Histol Histopathol 25:637-646
20. Hashimoto T, Tsuneki M, Foster T R, Santana J M, Bai H, Wang M, Hu H, Hanisch J J, Dardik A 2016 Membrane-mediated regulation of vascular identity. Birth Defects Res C Embryo Today 108:65-84
21. Martin-Almedina S, Martinez-Corral I, Holdhus R, Vicente A, Fotiou E, Lin S, Petersen K, Simpson M A, Hoischen A, Gilissen C, Jeffery H, Atton G, Karapouliou C, Brice G, Gordon K, Wiseman J W, Wedin M, Rockson S G, Jeffery S, Mortimer P S, Snyder M P, Berland S, Mansour S, Makinen T, Ostergaard P 2016 EPHB4 kinase-inactivating mutations cause autosomal dominant lymphatic-related hydrops fetalis. J Clin Invest 126:3080-3088
22. Kettleborough R N, Busch-Nentwich E M, Harvey S A, Dooley C M, de Bruijn E, van Eeden F, Sealy I, White R J, Herd C, Nijman I J, Fenyes F, Mehroke S, Scahill C, Gibbons R, Wali N, Carruthers S, Hall A, Yen J, Cuppen E, Stemple D L 2013 A systematic genome-wide analysis of zebrafish protein-coding gene function. Nature 496:494-497
23. Sun S, Chen S, Liu F, Wu H, McHugh J, Bergin I L, Gupta A, Adams D, Guan J L 2015 Constitutive Activation of mTORC1 in Endothelial Cells Leads to the Development and Progression of Lymphangiosarcoma through VEGF Autocrine Signaling. Cancer Cell 28:758-772.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating a lymphatic anomaly in a human patient, the method comprising:
   a) detecting in a biological sample from said patient, a nucleic acid comprising a single nucleotide variant (SNV), wherein the SNV is selected from:
      i) c.2334+1G>C in EPHB4;
      ii) c.3481A>G:p.S1161G in PIK3R4;
      iii) c.1393-7C>T in PIK3R6;
      iv) c.6818A>G:p.P2273L in mTOR; and
      v) c.640T>C:p.S214P in ARAF; and
   b) administering one or more agents suitable for treatment of said lymphatic anomaly to the patient, thereby treating the lymphatic anomaly,
      wherein said one or more agents suitable for treatment of said lymphatic anomaly are selected from the group consisting of one or more mTOR inhibitors, one or more PIK3K inhibitors, one or more MEK/ERK inhibitors, and a combination of one or more of any of said inhibitors.

2. The method of claim 1, wherein said one or more agents is selected from the group consisting of rapamycin, everolimus, AZD8055, temsirolimus, KU-0063794, MHY1485, BEZ235, PI-103, torkinib, tacrolimus, selumetinib, PD0325901, trametinib, pimasertib, AZD8330, binimetinib, SL-327, refametinib, cobimetinib, ridaforolimus, INK 128, voxtalisib, torin 1, omipalisib, OSI-027, PF-04691502, apitolisib, GSK1059615, gedatolisib, WYE-354, AZD2014, torin 2, WYE-125123, PP121, WYE-687, CH5132799, WAY-600, ETP-46464, GDC-0349, XL388, zotarolimus, BGT226, palomid 529, chrysophanic acid, TAK-733, and PD184352.

3. The method of claim 1, wherein the lymphatic anomaly is characterized by abnormal formation of lymphatic vessels and/or tissue overgrowth.

4. The method of claim 1, wherein the lymphatic anomaly is selected from lymphangiomatosis (LAM) or generalized lymphatic anomaly (GLA).

5. The method of claim 1, wherein the lymphatic anomaly is characterized by chylous effusions, including pericardial, pleural, or peritoneal effusions.

6. The method of claim 1, wherein the method further comprises generating a report identifying the SNV after detection in the biological sample and identifying suggested treatment(s) for the lymphatic anomaly based upon the SNV so identified.

7. The method of claim 1, wherein the treatment further comprises administering systemic chemotherapy, interferon alpha, radiotherapy, and/or surgery.

8. The method of claim 1, wherein the detecting comprises analyzing a polynucleotide sample to determine the presence of said SNV by performing a process selected from the group consisting of detection of specific hybridization, measurement of allele size, restriction fragment length polymorphism analysis, allele specific hybridization analysis, single base primer extension reaction, and sequencing of an amplified polynucleotide.

9. The method of claim 1, wherein the biological sample comprises DNA.

10. The method of claim 5, wherein said one or more MEK/ERK inhibitor is selected from Selumetinib (AZD6244), PD0325901, Trametinib (GSK1 120212), PD184352 (CI-1040), Pimasertib (AS-703026), TAK-733, AZD8330, Binimetinib (MEK162, ARRY-162, ARRY-438162), SL-327, Refametinib (RDEA119, Bay 86-9766), and Cobimetinib (GDC-0973, RG7420).

11. The method of claim 1, wherein a combination of agents is administered, said combination being selected from the group consisting of
   a) Ridaforolimus and Trametinib;
   b) Ridaforolimus and Selumetinib or Cobimetinib;
   c) BEZ235 and Selumetinib;
   d) Omipalisib and Selumetinib or Trametinib;
   e) Everolimus and Trametinib or Selumetinib;
   f) Sirolimus, Ridaforolimus and Selumetinib;
   g) Sirolimus, Ridaforolimus and Trametinib;
   h) Torkinib and Trametinib;
   i) BEZ235, Torkinib and Trametinib; and
   j) Sirolimus and Gedatolisib and Trametinib.

* * * * *

SEQUENCE LISTING

<160> NUMBER OF SEQ ID NOS: 15

<210> SEQ ID NO 1
<211> LENGTH: 44
<212> TYPE: DNA
<213> ORGANISM: Artificial Sequence
<220> FEATURE:
<223> OTHER INFORMATION: Primer 1 for insertion into EPHB4

<400> SEQUENCE: 1
tgggaatctt tcctccccc agcattagca gggagctagt gtag            44

<210> SEQ ID NO 2
<211> LENGTH: 44
<212> TYPE: DNA
<213> ORGANISM: Artificial Sequence

```
<220> FEATURE:
<223> OTHER INFORMATION: Primer 2 for insertion into EPHB4

<400> SEQUENCE: 2
ctacactagc tccctgctaa tgctgggggg aggaaagatt ccca                    44

<210> SEQ ID NO 3
<211> LENGTH: 35
<212> TYPE: DNA
<213> ORGANISM: Artificial Sequence
<220> FEATURE:
<223> OTHER INFORMATION: Forward amplification PCR primer

<400> SEQUENCE: 3
atgaattcgc caccatggag ctccgggtgc tgctc                              35

<210> SEQ ID NO 4
<211> LENGTH: 31
<212> TYPE: DNA
<213> ORGANISM: Artificial Sequence
<220> FEATURE:
<223> OTHER INFORMATION: Reverse amplification PCR primer

<400> SEQUENCE: 4
atgcggccgc tcagtactgc ggggccggtc c                                  31

<210> SEQ ID NO 5
<211> LENGTH: 35
<212> TYPE: DNA
<213> ORGANISM: Artificial Sequence
<220> FEATURE:
<223> OTHER INFORMATION: Forward FLAG insertion primer

<400> SEQUENCE: 5
gatgatgata aattggaaga gaccctgctg aacac                              35

<210> SEQ ID NO 6
<211> LENGTH: 30
<212> TYPE: DNA
<213> ORGANISM: Artificial Sequence
<220> FEATURE:
<223> OTHER INFORMATION: Reverse FLAG insertion primer

<400> SEQUENCE: 6
atctttataa tcagctgcag ccaacgaagc                                    30

<210> SEQ ID NO 7
<211> LENGTH: 19
<212> TYPE: DNA
<213> ORGANISM: Artificial Sequence
<220> FEATURE:
<223> OTHER INFORMATION: EPHB4 gRNA

<400> SEQUENCE: 7
ggtcgtaatg gtccctcga                                                19

<210> SEQ ID NO 8
<211> LENGTH: 25
<212> TYPE: DNA
<213> ORGANISM: Artificial Sequence
<220> FEATURE:
<223> OTHER INFORMATION: hEPHB4-F for assembly of gRNA

<400> SEQUENCE: 8
caccgcgagc tccctggtaa tgctg                                         25
```

```
<210> SEQ ID NO 9
<211> LENGTH: 25
<212> TYPE: DNA
<213> ORGANISM: Artificial Sequence
<220> FEATURE:
<223> OTHER INFORMATION: hEPHB4-R for assembly of gRNA

<400> SEQUENCE: 9
aaaccagcat taccagggag ctcgc                                            25

<210> SEQ ID NO 10
<211> LENGTH: 24
<212> TYPE: DNA
<213> ORGANISM: Artificial Sequence
<220> FEATURE:
<223> OTHER INFORMATION: hPIK3R6-F for assembly of gRNA

<400> SEQUENCE: 10
caccgcttct gggggaaagg ggat                                             24

<210> SEQ ID NO 11
<211> LENGTH: 25
<212> TYPE: DNA
<213> ORGANISM: Artificial Sequence
<220> FEATURE:
<223> OTHER INFORMATION: hPIK3R6-R for assembly of gRNA

<400> SEQUENCE: 11
aaaccatccc ctttccccca gaagc                                            25

<210> SEQ ID NO 12
<211> LENGTH: 179
<212> TYPE: DNA
<213> ORGANISM: Artificial Sequence
<220> FEATURE:
<223> OTHER INFORMATION: hEPHB4 Single-stranded donor oligonucleotides

<400> SEQUENCE: 12
accctcagcc tcccaccttt ccaacctgcc ctgcccacct ggccctaaga agctcacacc       60
cagtattacc cccagcatta gcaaagaact agtgtaggtg ggatcggaag agttctcctc      120
caggaatcgg gaaaggccaa agtcagacac tttgcagacg aggttgctgt tgactagga      179

<210> SEQ ID NO 13
<211> LENGTH: 23
<212> TYPE: DNA
<213> ORGANISM: Artificial Sequence
<220> FEATURE:
<223> OTHER INFORMATION: Primer 1 to generate P2273L mutant

<400> SEQUENCE: 13
gcggatggct ctggactatg acc                                              23

<210> SEQ ID NO 14
<211> LENGTH: 24
<212> TYPE: DNA
<213> ORGANISM: Artificial Sequence
<220> FEATURE:
<223> OTHER INFORMATION: Primer 2 to generate P2273L mutant

<400> SEQUENCE: 14
aacatgatgc gatgctcgat gttg                                             24
```

```
<210> SEQ ID NO 15
<211> LENGTH: 25
<212> TYPE: DNA
<213> ORGANISM: Artificial Sequence
<220> FEATURE:
<223> OTHER INFORMATION: Morpholino sequence targeting exon 13 of EPHB4

<400> SEQUENCE: 15
cgagagcagt atttaccagt gagct                                              25
```